(12) United States Patent
Fritz et al.

(10) Patent No.: US 6,391,575 B1
(45) Date of Patent: May 21, 2002

(54) METHODS FOR DETECTING MEMBRANE DERIVED CASPASE ACTIVITY AND MODULATORS THEREOF

(75) Inventors: Lawrence C. Fritz, Rancho Santa Fe; Joseph F. Krebs, San Diego, both of CA (US)

(73) Assignee: IDUN Pharmaceuticals, Inc., San Diego, CA (US)

( * ) Notice: Subject to any disclaimer, the term of this patent is extended or adjusted under 35 U.S.C. 154(b) by 0 days.

(21) Appl. No.: 09/263,590

(22) Filed: Mar. 5, 1999

(51) Int. Cl.[7] .............................. C12Q 1/37; C12N 9/50
(52) U.S. Cl. ......................... 435/23; 435/219; 435/7.72
(58) Field of Search .......................... 435/23, 219, 7.72

(56) References Cited

U.S. PATENT DOCUMENTS 5,837,837 A * 11/1998 Hunter et al. ............... 536/23.1

FOREIGN PATENT DOCUMENTS

| | | |
|---|---|---|
| WO | WO 98/02579 | 1/1998 |
| WO | WO 98/10778 | 3/1998 |
| WO | WO 00/04914 | 2/2000 |

OTHER PUBLICATIONS

Talanian et al. Substrate specificities of Caspase Family Proteases, J. Biol. Chem. 272(15): 9677–9682, Apr. 11, 1997.*

Villa et al., Caspases and Caspase Inhibitors, TIBS 22:388–393, Oct. 1997.*

Virkajarvi et al., Apoptotic index and apoptosis influencing proteins bcl–2, mcl–1, bax and caspases 3, 6 and 8 in pancreatic carcinoma, Histopathology 33: 432–439, Nov. 1998.*

Derwent WPI Acc. No. 2000–001088/200001, abstract of EP 955 377 A1, Nov. 10, 1999.

Akita et al., "Involvement of Caspase–1 and Caspase–3 in the Production and Processing of Mature Human Interleukin 18 in Monocytic THP.1 Cells" *The Journal of Biological Chemistry* 272(42): 26595–26603, 1997.

Armstong et al., "Fas–Induced Activation Of The Cell Death–Related Protease CPP32 Is Inhibited By Bcl–2 and By ICE Family Protease Inhibitors," *The Journal of Biological Chemistry* 271(25): 16850–16855, 1996.

Enari et al., "A Caspase–Activated DNase That Degrades DNA During Apoptosis, and Its Inhibitor ICAD," *Nature* 391: 43–50, 1998.

Enari et al., "Apoptosis By A Cytosolic Extract From Fas–Activated Cells," *The EMBO Journal* 14(21): 5201–5208, 1995.

Farschon et al., "Temporal Phases in Apoptosis Defined by the Actions of Src Homology 2 Domains, Ceramide, Bcl–2, Interleukin–1 β Converting Enzyme Family Proteases, and a Dense Membrane Fraction," *The Journal Of Cell Biology* 137(5): 1117–1125, 1997.

Fattman et al., "Characterization of Interior Cleavage of Retinoblastoma Protein in Apoptosis," *Journal of Cellular Biochemistry* 67: 399–408, 1997.

Han et al., "A Sequential Two–Step Mechanism for the Production of the Mature p17:p12 Form of Caspase–3 in Vitro," *The Journal of Biological Chemistry* 272(20): 13432–13436, 1997.

Han et al., "DNA–Dependent Protein Kinase Is A Target For a CPP32–Like Apoptotic Protease," *The Journal of Biological Chemistry* 271(40): 25035–25040, 1996.

Jemmerson et al., "A Conformational Change in Cytochrome c of Apoptotic and Necrotic Cells Is Detected by Monoclonal Antibody Binding Mimicked by Association of the Native Antigen with Synthetic Phospholipid Vesicles," *Biochemistry* 38: 3599–3609, 1999.

Karanewsky et al., "Conformationally Constrained Inhibitors Of Caspase–1 (Interleukin–1β Converting Enzyme) And Of The Human CED–3 Homologue Caspase–3 (CPP32, Apopain)" *Bioorganic & Medicinal Chemistry Letters* 8: 2757–2762, 1998.

Kitamura et al., "Alteration of Proteins Regulating Apoptosis, Bcl–2, Bcl–x, Bax, Bak, Bad, ICH–1 and CPP32, in Alzheimer's Disease," *Brain Research* 780: 260–269, 1998.

Krebs et al., "Activation of Membrane–Associated Procaspase–3 Is Regulated by Bcl–2," *The Journal of Cell Biology* 144(5): 915–926, 1999.

Martin et al., "Cell–Free Reconstitution of Fas–, UV Radiation– And Ceramide–Induced Apoptosis," *The EMBO Journal* 14(21): 5191–5200, 1995.

Mitamura et al., "Cytosolic Nuclease Activated by Caspase–3 and Inhibited by DFF–45," *Biochemical and Biophysical Research Communications* 243: 480–484, 1998.

Newmeyer et al., "Cell–Free Apoptosis in Xenopus Egg Extract: Inhibition by Bcl–2 and Requirement for an Organelle Fraction Enriched in Mitochondria," *Cell* 79: 353–364, 1994.

Nicholson et al., "Identification and Inhibition of the ICE/CED–3 Protease Necessary For Mammalian Apoptosis," *Nature* 376: 37–43, 1995.

Srinivasan et al., "Bcl–2 Expression in Neural Cells Blocks Activation of ICE/CED–3 Family Proteases During Apoptosis," *The Journal of Neuroscience* 16(18): 5654–5660, 1996.

Virkajärvi et al., "Apoptotic Index and Apoptosis Influencing Proteins Bcl–2, Mcl–1, Bax and Caspases 3, 6 and 8 in Pancreatic Carcinoma," *Histopathology* 33: 432–439, 1998.

* cited by examiner

Primary Examiner—Rebecca E. Prouty
Assistant Examiner—Richard Hutson
(74) *Attorney, Agent, or Firm*—SEED Intellectual Property Law Group PLLC

(57) ABSTRACT

Provided are methods for detecting membrane derived apoptotic activity. In one embodiment, the present invention provides methods for identifying membrane derived caspase activity. In other embodiments, drug discovery methods are provided for screening compounds that inhibit or enhance membrane derived caspase activity. In the various embodiments, heavy membrane fractions are utilized for the screening methodologies described herein.

13 Claims, 8 Drawing Sheets

METHODS FOR DETECTING MEMBRANE DERIVED CASPASE ACTIVITY AND MODULATORS THEREOF

TECHNICAL FIELD

The present invention relates generally to methods for detecting membrane derived caspase activity and modulators thereof, and more particularly to novel cell-free screening assays for identifying inhibitors and enhancers of membrane derived caspase activity.

BACKGROUND OF THE INVENTION

Tissue homeostasis is maintained by the process of apoptosis—that is, the normal physiological process of programmed cell death. Changes to the apoptotic pathway that prevent or delay normal cell turnover are often as important in the pathogenesis of diseases as are abnormalities in the regulation of the cell cycle. Like cell division, which is controlled through complex interactions between cell cycle regulatory proteins, apoptosis is similarly regulated under normal circumstances by the interaction of gene products that either function to prevent or induce cell death.

Since apoptosis functions in maintaining tissue homeostasis in a range of physiological processes, such as embryonic development, immune cell regulation and normal cellular turnover, the dysfunction or loss of regulated apoptosis can lead to a variety of pathological disease states. For example, the loss of apoptosis can lead to the accumulation of self-reactive lymphocytes associated with many autoimmune diseases. Inappropriate loss or inhibition of apoptosis can also lead to the accumulation of virally infected cells and hyperproliferative cells, such as neoplastic or tumor cells. Similarly, the inappropriate activation of apoptosis can contribute to a variety of pathological disease states including, for example, acquired immunodeficiency syndrome (AIDS), neurodegenerative diseases and ischemic injury.

Although apoptosis is mediated by diverse signals and complex interactions of cellular gene products, the results of these interactions ultimately feed into a cell death pathway that is evolutionarily conserved between humans and invertebrates. The pathway, itself is a cascade of proteolytic events analogous to that of the blood coagulation cascade.

Several gene families and products that modulate the apoptotic process have now been identified. One family is the aspartate-specific cysteine proteases ("caspases"). The caspase Ced-3, identified in *C. elegans,* is required for programmed cell death during development of the roundworm *C. elegans.* Ced-3 homologues as well as other caspases have been characterized. The human caspase family includes, for example, Ced-3, human ICE (interleukin-1-β converting enzyme) (caspase-1), ICH-1 (caspase-2), CPP32 (caspase-3), $ICE_{rel}II$ (caspase-4), $ICE_{rel}III$ (caspase-5), Mch2 (caspase-6), ICE-LAP3 (casepase-7), Mch5 (caspase-8), ICE-LAP6 (caspase-9), Mch4 (caspase-10), caspase-11, caspase-12, caspase-13, caspase-14, and others.

The caspase family of cysteine proteases are essential effectors of the apoptotic process (Yuan et al., *Cell* 75:641–652, 1993; Alnemri et al., *Cell* 87:171, 1996; Cohen, *Biochem.* 326:1–16, 1997; Miller, *Semin. Immunol* 9:35–49, 1997; Salvesen and Dixit, *Cell* 91:443–446, 1997). Caspases are synthesized as inactive zymogens, which are activated by proteolytic processing to yield large (~18 kDa) and small (~12 kDa) subunits that associate to form active enzymes (Thornberry et al., *Nature* 396:768–774, 1992; Nicholson et al., *Nature* 376:37–43, 1995; Stennicke and Salvesen, *J. Biol. Chem.* 272:25719–25723, 1997). Diverse apoptotic stimuli cause the activation of specific caspases which then initiate a protease cascade by proteolytically processing additional caspases (Srinivasula et al., *Proc. Natl. Acad. Sci. USA* 93:14486–14491, 1996; Yu et al., *Cancer Res.* 58:402–408, 1998). Once activated, these downstream (executioner) caspases kill cells by cleaving specific molecular targets that are essential for cell viability or by activating pro-apoptotic factors (Liu et al., *Cell* 89:175–184, 1997; Enari et al., *Nature* 391:43–50, 1998; Salvesen and Dixit, *Cell* 91:443–446, 1997). Although caspases have been generally shown to be cytosolic proteins (Miller et al., *J. Biol. Chem.* 268:18062–18069, 1993; Nicholson et al., *Nature* 376:37–43, 1995; Li et al., *J. Biol. Chem.* 272:30299–30305, 1997), immunochemical studies have suggested that in some instances, caspases might also be associated with the nucleus or plasma membrane (Singer et al., *J. Exp. Med.* 182:1447–1459, 1995; Krajewski et al., *Blood* 89:3817–3825, 1997; Posmantur et al., *J. Neurochem.* 68:2328–2337, 1997). Recently published data has also indicated an association of certain caspases with mitochondria and endoplasmic reticulum (Mancini et al., *J. Cell Biol.* 140:1485–1495, 1998; Chandler et al., *J. Biol. Chem.* 273:10815–10818, 1998).

The Bcl-2 family constitutes another key set of regulators of the apoptotic pathway. These proteins can function to modulate apoptosis in a wide variety of cell systems (Oltvai and Korsmeyer, *Cell* 79:189–192, 1994; Reed, *Nature* 387:773–776, 1997). Bcl-2 family proteins contain one to four conserved domains, designated BH1-BH4, and most family members contain a carboxyl-terminal transmembrane anchor sequence which allows them to be associated with cellular membranes including the outer membrane of the mitochondria, the nuclear envelope and the endoplasmic reticulum (Reed, *Nature* 387:773–776, 1997; Krajewski et al., *Cancer Res.* 53:4701–4714, 1993; Yang et al., *J. Cell. Biol.* 128:1173–1184, 1995; Lithgow et al., *Cell Growth Differ* 3:411–417, 1994). The over-expression of Bcl-2 has been shown to inhibit the activation of cytoplasmic caspases following apoptoic stimuli in several cell systems (Armstrong et al., *J. Biol. Chem.* 271:16850–16855, 1996; Chinnaiyan et al., *J. Biol. Chem.* 271:4573–4576, 1996; Boulakia et al., *Oncogene* 12:29–36, 1996; Srinivasan et al., *J. Neurosci.* 16:5654–60, 1996). Moreover, previous work has demonstrated that Bcl-2 inhibits the onset of apoptosis, but once apoptosis is initiated, Bcl-2 does not impede the process (McCarthy et al., *J. Cell Biol.* 136:215–217, 1997). However, it remains unclear how the membrane bound Bcl-2 exerts control over the soluble cytoplasmic caspases. Further, no suitable methods exist for studying membrane bound Bcl-2 and its effects on caspase activity in a cell free manner.

The identification of compounds that modulate the apoptotic pathway via enhancement or inhibition of membrane derived caspase activity has been hindered by the lack of such methods. Available methods are limited by the lack of specificity, efficiency, and/or utilization of whole cells or cytoplasmic extracts thereof. For example, most anti-cancer drugs are screened for their ability to kill cells and therefore will identify compounds that induce both necrosis or apoptosis. In addition, many other assay techniques focus on studying the inhibition or enhancement of caspase enzymes located further into the cascade. Therefore, there exists a need in the art for methods of identifying compounds that not only inhibit or enhance cell death, but also compounds that modulate the initiation of the apoptotic cascade. The present invention fulfills this need, while further providing other related advantages.

The foregoing characteristics, and others which shall be described in greater detail below, make the methodologies described herein particularly attractive for drug discovery applications.

SUMMARY OF THE INVENTION

The present invention generally provides methods for detecting membrane derived caspase activity and methods for identifying modulators thereof. In one aspect, the invention provides a method for identifying membrane derived caspase activity, that includes, incubating a membrane fraction comprising heavy or nuclear membranes under conditions and for a time sufficient to allow for the evolution of caspase activity, and subsequently detecting caspase activity.

In another aspect, the present invention provides a method for identifying an inhibitor of the activity of a membrane derived caspase, that includes, contacting a membrane fraction with a caspase substrate in the presence and absence of at least one candidate inhibitor; and comparing the levels of caspase substrate turnover, and therefrom identifying an inhibitor of the activity of a membrane derived caspase.

In yet another aspect, the present invention provides a method for identifying an enhancer of the activity of a membrane derived caspase, that includes, contacting a membrane fraction with a caspase substrate in the presence and absence of at least one candidate enhancer; and comparing the levels of caspase substrate turnover, and therefrom identifying an enhancer of the activity of a membrane derived caspase.

A further aspect of the present invention is a method for identifying an inhibitor or enhancer of the evolution of caspase processing within a membrane fraction, that includes, contacting a membrane fraction with at least one candidate inhibitor or candidate enhancer; and detecting the presence of large and small caspase subunits, and therefrom determining the level of caspase processing, wherein a decrease in processing indicates the presence of a caspase processing inhibitor, and wherein an increase in processing indicates the presence of a caspase processing enhancer.

In other embodiments, the present invention provides a method of identifying a compound that modulates membrane fraction derived caspase activity, that includes, incubating a membrane fraction, an inhibitor of apoptosis, and a caspase substrate in the presence and absence of at least one candidate compound under conditions and for a time sufficient to allow for the evolution of caspase activity; and comparing the levels of caspase substrate turnover, thereby identifying a compound that modulates membrane derived caspase activity.

In other embodiments, inhibitors and enhancers of the activity of a membrane derived caspase that are identified by the various methods are provided.

In the various embodiments, caspase activity is detected by measuring substrate turnover or caspase processing. In other embodiments, substrate turnover is measured by time course or endpoint analysis. In further embodiments, the membrane fraction comprises heavy or nuclear membranes. In yet further embodiments, the membrane fraction is derived from cells expressing an anti-apoptotic polypeptide. In even further embodiments, the membrane fraction is derived from non-apoptotic cells.

These and other aspects of the present invention will become evident upon reference to the following detailed description and attached drawings. In addition, the various references set forth below that describe in more detail certain procedures or compositions (e.g., plasmids, etc.), and are therefore incorporated by reference in their entirety.

BRIEF DESCRIPTION OF THE DRAWINGS

FIG. 3A illustrates the spontaneous activation of caspase activity in heavy membrane from 697-neo and 697-Bcl-2 cells as a function of DEVD-amc turnover. FIG. 3B illustrates the generation of soluble caspase activity from membranes as a function of DEVD-amc turnover.

FIG. 6A illustrates the caspase activity present in the heavy membrane fraction. FIG. 6B illustrates the caspase activity present in the cytoplasmic fraction.

FIG. 7A is a graph demonstrating the effects of NP-40 on spontaneous and induced caspase activities in neo-membranes. FIG. 7B is a graph illustrating the effect of NP-40 on spontaneous caspase activation in Bcl-2 and neo-membranes. FIG. 7C is a graph depicting NP-40-dependent and independent activation of procaspase-3 by granzyme B treatment of mitochondrial enriched fractions.

DETAILED DESCRIPTION OF THE INVENTION

Figure 1:
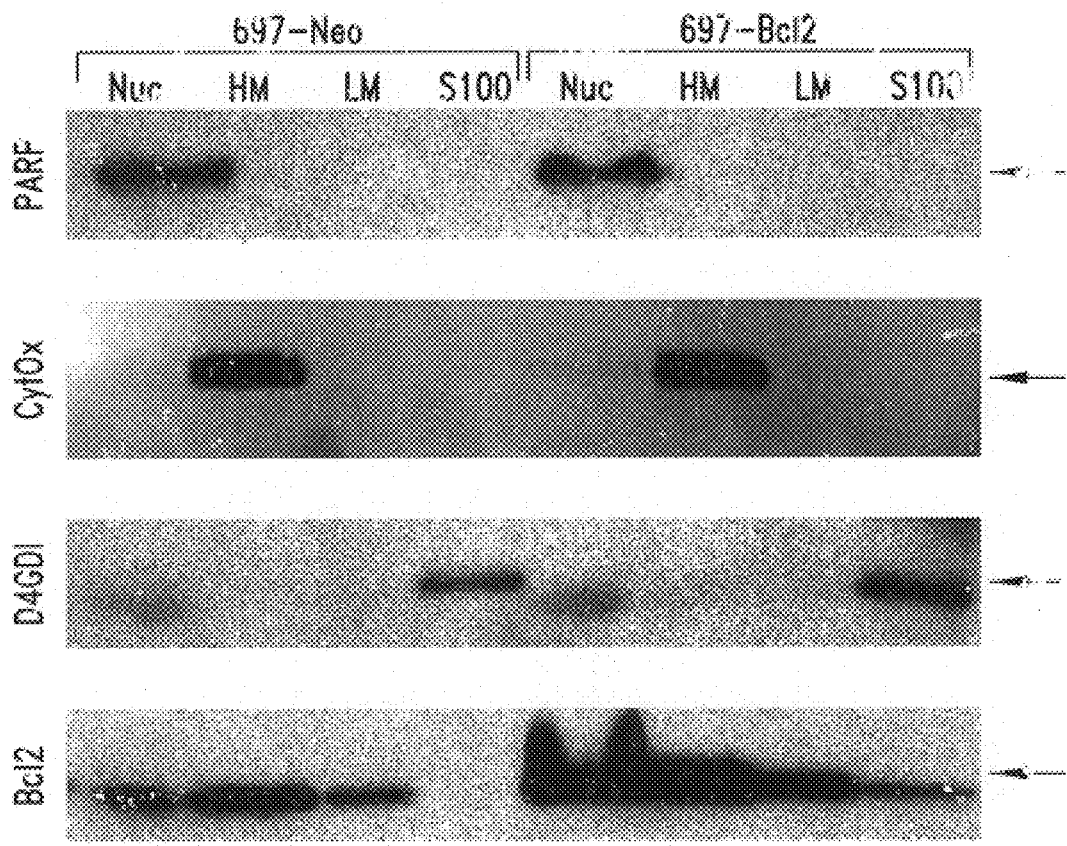
FIG. 1 is a scanned image of an immunoblot representing SDS-PAGE analysis of subcellular fractions from 697-neo and 697-Bcl-2 cells using antibodies to PARP, cytochrome oxidase (subunit IV), D4GDI and Bcl-2. Nuc=nuclear fraction, HM=heavy membrane fraction, LM=light membrane fraction, S100=cytosolic fraction. Arrows indicate the specific immunoreactive band.

As noted above, the present invention is generally directed to methods of detecting and modulating membrane derived caspase activity. One application of the disclosed invention is in the identification of inhibitors or enhancers of apoptosis. In simple terms, the use of such a novel cell-free assay system provides a means for identifying compounds which promote or inhibit programmed cell death at a critical initiation point (i.e., membranes). Another aspect of the subject invention is the ability of the disclosed assay system to investigate the effects of membranes derived from cells over-expressing apoptotic pathway proteins, such as those of the bcl-2 family.

As described herein, a preferred assay system utilizes heavy or nuclear membranes for detecting membrane derived caspase activity and/or for identifying compounds that modulate caspase activity, directly or indirectly, in a cell-free system. Therefore, by using such membrane systems, control points upstream of the cytoplasmic apoptotic pathway can be effectively assayed and modulators thereof may be identified.

The assay methods of the present invention are particularly useful for drug discovery, in part by use of high throughput methodologies. Accordingly, by utilizing the cell-free assay system of the present invention, identification of compounds that affect evolution of caspase activity from the membrane fraction is rapidly achieved.

Prior to setting forth the invention, it may be helpful to an understanding thereof to set forth definitions of certain terms that will be used hereinafter.

As used herein, a "caspase" refers to a cysteine protease that specifically cleaves proteins after Asp residues. Caspases are initially expressed as zymogens, in which a large subunit is N-terminal to a small subunit. Caspases are generally activated by cleavage at internal Asp residues. These proteins have been identified in many eukaryotes, including C. elegans, Drosophila, mouse, and human. Currently, there are at least 14 known caspase genes, named caspase-1 through caspase-14. Table 1 recites ten human caspases along with their alternative names.

| Caspase | Alternative name |
| --- | --- |
| Caspase-1 | ICE |
| Caspase-2 | ICH-1 |
| Caspase-3 | CPP32, Yama, apopain |
| Caspase-4 | $ICE_{rel}II$; TX, ICH-2 |
| Caspase-5 | $ICE_{rel}III$; TY |
| Caspase-6 | Mch2 |
| Caspase-7 | Mch3, ICE-LAP3, CMH-1 |
| Caspase-8 | FLICE; MACH; Mch5 |
| Caspase-9 | ICE-LAP6; Mch6 |
| Caspase-10 | Mch4, FLICE-2 |

Within the context of this invention, it should be understood that a caspase includes wild-type protein sequences, as well as other variants (including alleles) of the native protein sequence. Briefly, such variants may result from natural polymorphisms or may be synthesized by recombinant methodology, and differ from wild-type protein by one or more amino acid substitutions, insertions, deletions, or the like. Typically, when engineered, amino acid substitutions will be conservative, i.e., substitution of amino acids within groups of polar, non-polar, aromatic, charged, etc. amino acids. In the region of homology to the native sequence, variants should preferably have at least 90% amino acid sequence identity, and within certain embodiments, greater than 92%, 95%, or 97% identity. Such amino acid sequence identity may be determined by standard methodologies, including use of the National Center for Biotechnology Information BLAST search methodology available at www.ncbi.nlm.nih.gov. The identity methodologies preferred are those described in U.S. Pat. No. 5,691,179 and Altschul et al., Nucleic Acids Res. 25:3389–3402, 1997 all of which are incorporated herein by reference. If Gapped BLAST 2.0 is utilized, then it is utilized with default settings.

As will be appreciated by those skilled in the art, a nucleotide sequence encoding a caspase or variant may differ from the known native sequences, due to codon degeneracies, nucleotide polymorphisms, or amino acid differences. In other embodiments, variants should preferably hybridize to the native nucleotide sequence at conditions of normal stringency, which is approximately 25–30° C. below Tm of the native duplex (e.g., 5×SSPE, 0.5% SDS, 5X Denhardt's solution, 50% formamide, at 42° C. or equivalent conditions; see generally, Sambrook et al. *Molecular Cloning: A Laboratory Manual*, 2nd ed., Cold Spring Harbor Press, 1987; Ausubel et al., *Current Protocols in Molecular Biology*, Greene Publishing, 1987).

An "isolated nucleic acid molecule" refers to a polynucleotide molecule in the form of a separate fragment or as a component of a larger nucleic acid construct, that has been separated from its source cell (including the chromosome it normally resides in) at least once in a substantially pure form. Nucleic acid molecules may be comprised of a wide variety of nucleotides, including DNA, RNA, nucleotide analogues, or some combination of these.

A "membrane fraction", as used herein, refers to a subcellular fraction of a eukaryotic cell comprising cellular membranes. In particular, the term "heavy membranes", as used herein, refers to a subcellular fraction substantially free of nuclear and light membranes, wherein one of the predominant components is mitochondria.

A "stimulator of apoptosis" or "pro-apoptotic agent", as used herein refers to an agent that increases the specific apoptotic activity of a cell. Illustrative examples of such stimulus are deprivation of a growth factor, Fas ligand, anti-Fas antibody, staurosporine, ultraviolet irradiation, gamma irradiation, tumor necrosis factor, and others well known in the art. Accordingly, a stimulator of apoptosis is an agent that increases the molecular activity of caspase molecules either directly or indirectly. In addition, a stimulator of apoptosis can be a polypeptide that is capable of increasing or inducing the apoptotic activity of a cell. Such polypeptides include those that directly regulate the apoptotic pathway such as Bax, Bad, Bcl-xS, Bak, Bik, and active caspases as well as those that indirectly regulate the pathway.

An "inhibitor of apoptosis" or "anti-apoptotic agent", as used herein refers to an agent that decreases the apoptotic activity of a cell when compared to control agents. Illustrative examples of such anti-apoptotic agents include small molecules, fink, p35, crmA, Bcl-2, $Bcl-X_L$, Mcl-1, E1B-19K from adenovirus, as well as antagonists of pro-apoptotic agents (e.g., antisense, ribozymes, antibodies, etc.).

Accordingly, an inhibitor of apoptosis is an agent that decreases the molecular activity of caspase molecules either directly or indirectly.

An "apoptotic pathway protein", as used herein refers to a protein involved in the cell death pathway. Illustrative examples include Bcl-2, $Bcl-X_s$, $Bcl-X_L$, Bik, Bak, Bax, Bad, caspase molecules, Apaf-1, cytochrome c, and the like.

"Evolution of caspase activity", as used herein, refers to the increasing of detectable levels of caspase protease activity over a time period. Such evolution may be evidenced by detectable increases in substrate turnover (e.g., fluorogenic substrates) and/or detectable increases in caspase processing.

"Membrane derived caspase activity", as used herein, refers to caspase activity that is released from or associated with heavy or nuclear membranes.

A. Membrane Preparations

Membrane preparations within the context of the present invention may be derived from a variety of cell types or sources. Typically, for ease of handling, the cells utilized will be a eukaryotic cell line or other culturable cell type. However, cells can also be derived from tissues and other non-cultured sources. One of ordinary skill in the art would readily appreciate that the assays of the present invention are not dependent upon the exact source or type of cell from which membrane fractions are prepared.

Subcellular fractionation has been a basic research tool in cell biology for the last 30 years. Accordingly, those of ordinary skill in the art are familiar with various techniques for such fractionation. Typically, subcellular fractionation comprises two basic steps, 1) homogenization and 2) separation. Homogenization in its ideal form allows particulate organelles such as the nucleus, mitochondria, lysosomes, and peroxisomes to remain intact. A variety of homogenization techniques are known, such as Dounce homogenizers (glass/glass), Potter-Elvehjem homogenizers (glass/teflon), repeated pipetting, passage through small gauge needle, and the like. Exemplary techniques are described in detail by Harms et al., *Proc. Natl. Acad. Sci. USA* 77:6139–6143 1980, Darte et al. *J. Exp. Med.* 157:1208–1228, 1983, and Balch et al., *Cell* 39:405–416, 1984.

Separation of subcellular fractions is traditionally performed using density gradients. While sucrose gradients are the most widely used, many other alternatives are available (e.g., Ficoll, Percoll, Metrizamide, and Nycodenz) (see Methods in Enzymology Vol. 31, Part A (Flescher and Packer eds.), 1974). In addition, a number of alternative methods have been developed for isolation of various components, including density modification, free flow electrophoresis, and immuno-isolation (see Cell free Analysis of Membrane Traffic, pp. 35–127, (Morre et al. eds.) (1988)). Moreover, a variety of references are available which detail a multitude of fractionation techniques, for example, see Methods in Enzymology Vol. 31, Part A (Flescher and Packer eds.), 1974; Partition of Cell Particles and Macromolecules: Separation and purification of Biomolecules, Cell Organelles, Membranes, and Cells (Albertsson, ed.), 1986; Martin et al. *Eur. J. Clin. Inv.* 13:49–56, 1983.

An exemplary method of cellular fractionation comprises suspending cells in a hypotonic buffer in which a variety of protease inhibitors are present (e.g., PMSF, leupeptin, pepstatin, aprotinin, EDTA, etc.). The samples are incubated on ice, then homogenized using a Dounce homogenizer. Following homogenization the homogenate is centrifuged at 500×g to separate nuclei. The nuclear pellet can then be washed and resuspended. The supernatant is then centrifuged at 14,000×g for 30 minutes to pellet the heavy membranes. The 14,000×g supernatant can then be centrifuged at 100,000×g for 30 minutes to yield a supernatant (cytoplasmic fraction) and a pellet (light membrane fraction). The pelleted fractions can then be washed and resuspended in the appropriate buffer for assaying.

B. Screening of Inhibitors and Enhancers of the Evolution of Caspase Activity from a Membrane Fraction 1. Inhibitors and Enhancers of Membrane Derived Caspase Activity Candidate inhibitors and enhancers may be isolated or procured from a variety of sources, such as bacteria, fungi, plants, parasites, libraries of chemicals, peptides or peptide derivatives and the like. Inhibitors and enhancers may be also be rationally designed, based on the protein structure determined from X-ray crystallography (see, Mittl et al, *J. Biol. Chem.*, 272:6539–6547, 1997). In certain embodiments, the inhibitor targets a specific caspase (e.g., membrane associated caspases). In other embodiments, the candidate inhibitor or enhancer indirectly affects the release/evolution of membrane derived caspase activity.

Without being held to a particular mechanism, the inhibitor may act by preventing processing of a caspase, preventing caspase enzymatic activity, by other mechanisms, or by preventing liberation of the caspase from the membrane. Accordingly, the inhibitor may act directly or indirectly. In one embodiment, inhibitors interfere in the processing of the caspase protein. In other embodiments, the inhibitors are small molecules. In yet another embodiment, inhibitors interact with Bcl-2. In other aspects, the inhibitors prevent apoptosis. Inhibitors should have a minimum of side effects and are preferably non-toxic. Inhibitors that can penetrate cells are preferred.

In addition, enhancers of caspase activity or expression are desirable in certain circumstances. At times, increasing apoptosis will have a therapeutic effect. For example, tumors or cells that mediate autoimmune diseases are appropriate cells for destruction. Enhancers may increase the rate or efficiency of caspase processing, increase transcription or translation, increase caspase release/evolution from the membrane, or act through other mechanisms. As is apparent to one skilled in the art, many of the guidelines presented above apply to the design of enhancers as well.

2. Screening Assay Formats

Screening assays for inhibitors and enhancers will vary according to the type of inhibitor or enhancer and the nature of the activity that is being affected. In general, assays, within the context of the present invention, are designed to evaluate caspase protein processing or caspase enzymatic activity as the result of caspase activity that evolves/derives from a membrane fraction. In any of the assays, a statistically significant increase or decrease compared to a proper control is indicative of enhancement or inhibition. Moreover, it should be understood that detection of membrane derived caspase activity may be by direct or indirect means. For example, a direct means is detecting membrane caspase substrate turnover, while an indirect means is detecting the processing or direct activity of a caspase activated by the membrane derived caspase.

In one embodiment, the assay utilizes membrane preparations from eukaryotic cells. In this regard, any cell type may be used depending on the purpose of the assay. In certain embodiments, the membrane fraction comprises heavy membranes and/or nuclear membranes. In one aspect, the membrane fraction is contacted or contacted and incubated in the presence or absence of a candidate inhibitor or enhancer and the substrate turnover or caspase-processing is measured. Substrate turnover or caspase-processing (cleavage of caspases into large and small subunits) can be assessed by a variety of methods known by those of skill in the art including, for example, fluorescence spectroscopy, mass spectroscopy, HPLC, colorimetry (e.g., UV and visible spectroscopy), fluorography, radiography, gel electrophoresis, immuno-blotting/immuno-affinity, chromatography, N-terminal peptide sequencing and the like. Moreover, one of ordinary skill in the art will recognize that incubation may be carried out at a variety of temperatures, depending on the kinetics to be studied. In one embodiment, the incubation temperature is from 20° C. to 40° C. In other embodiments, the incubation temperature is from 25° C. to 37° C.

One in vitro assay can be performed by examining the effect of a candidate compound on the processing of a caspase (e.g., a pro-caspase or other protein substrate of a caspase) into two subunits. Briefly, a substrate (e.g., peptide, protein, or peptide mimetic) containing the enzyme recognition site of membrane derived caspase-3 is utilized (e.g., DEVD), for example, when such a substrate is a protein or peptide, the substrate is in vitro translated or purified from a cell expression system. This primary product is contacted or contacted and incubated with the membrane fraction in the presence or absence of a candidate inhibitor or enhancer and assessed for appearance of the two subunits. To facilitate detection, typically, the protein or peptide is labeled during translation or via gene fusion prior to expression. If radiolabeled, the two subunits may be readily detected by autoradiography after gel electrophoresis. One skilled in the art will recognize that other methods of labeling and detection may be used alternatively.

An alternative in vitro assay is designed to measure cleavage of a caspase substrate analog (e.g., Acetyl-DEVD-aminomethylcoumarin (amc), lamin, poly-(ADP-ribose) polymerase (PARP), and the like, a variety of which are commercially available). Substrate turnover (e.g., substrate hydrolysis) may be assayed using either comparison of timecourse (i.e., progress curve) assays (e.g., evolution of activity and substrate hydrolysis rate analysis via steady-state rate comparison) or endpoint analysis (e.g., final fluorescence minus initial fluorescence). Briefly, in this assay the membrane fraction is incubated with a candidate inhibitor or enhancer along with the caspase substrate. Detection of cleaved substrate is performed by any one of a variety of standard methods. Generally, the substrate will be labeled and followed by an appropriate detection means.

Typical substrates utilized within the context of the present invention include those agents whose turnover measures, directly or indirectly, the apoptotic pathway and, in particular, the enzymatic activity of one or more caspase molecules. In this regard a variety of substrates such as labeled caspase molecules, lamin, PARP and caspase substrate analogues are known by those of skill in the art. Such substrates are also available commercially from such companies as Oncogene Research Products, Cambridge, Mass. Illustrative substrate analogues which are tagged with fluorescent markers include, ZEVD-amc (carbobenzoxy-Glu-Val-Asp-aminomethylcoumarin), YVAD-amc (Acetyl-Tyr-Val-Ala-Asp-aminomethylcoumarin), and DEVD-amc (Acetyl-Asp-Glu-Val-Asp-aminomethylcoumarin).

Moreover, any known enzymatic analysis can be used to follow the inhibitory or enhancing ability of a candidate compound with regard to membrane derived caspase activity. It would be apparent to one of ordinary skill in the art that the candidate inhibitor or enhancer may be incubated with the cell prior to fractionation or with the membrane fraction after fractionation, but prior to detection. Moreover, the candidate inhibitor or enhancer may be contacted or contacted and incubated with the membrane fraction concurrently with a caspase substrate.

The assays briefly described herein may be used to identify an enhancer or inhibitor that specifically affects membrane derived caspase activity. A variety of methodologies exist that can be used to investigate the effect of a candidate compound. Such methodologies are those commonly used to analyze enzymatic reactions and include, for example, SDS-PAGE, spectroscopy, HPLC analysis, autoradiography, chemiluminescence, chromogenic reactions, and immunochemistry (e.g., blotting, precipitating, etc.).

Furthermore, in other assay embodiments, eukaryotic promoters may be utilized within a construct for delivering either inducible or constitutively expressed pro- or anti-apoptotic proteins to the cells from which membrane preparations will be derived. For example, cells can be transfected such that they overexpress the anti-apoptotic polypeptide Bcl-2, thereby providing cells wherein membrane preparations would have a higher level of Bcl-2, such that only enhancers of apoptosis which were capable of overcoming Bcl-2 inhibition would be detected. In this same regard, such cells could be treated with a stimulus of apoptosis such that the cell is "poised" for apoptosis prior to subfractionation. In such a method, treatment of the membrane fraction with an apoptotic pathway enhancer results in significantly more robust activation rate than a comparable enhancer effect on non-poised cells.

In further embodiments, cells "poised" for cell death by delivery of an apoptotic stimulator prior to subfractionation, may be created by treating cells that do not overexpress anti-apoptotic polypeptides, but which are fractionated prior to apoptosis. Such cells may be subfractionated and the membranes derived therefrom utilized for assaying candidate inhibitors and enhancers.

The methods described above for identification of inhibitors and enhancers of apoptosis provides an alternative format for measuring apoptotic activity, in that a cell is treated so that it is "poised" for programmed cell death. In this way the cell has synthesized and/or activated all necessary components that are required for programmed cell death. All that is required is a stimulus to cause the cell to extend past its holding point and into apoptosis. Accordingly, an enhancer would cause the cell to progress into programmed cell death, while an inhibitor would delay or suppress this progress in the presence of an apoptotic stimulus.

The holding point which prevents the cell from proceeding into programmed cell death can be the overexpression of a cell survival polypeptide or treatment of the cells with known apoptotic inhibitors. Cell survival polypeptides are characterized in that they exhibit the ability to prevent apoptosis when expressed or activated in a cell induced to undergo apoptosis. For example, in the absence of a functioning cell survival polypeptide, a cell treated with an apoptotic enhancer (e.g., a pro-apoptotic agent) will initiate or accelerate apoptosis. However, in the presence of a cell survival polypeptide, treatment with a pro-apoptotic agent/enhancer can initiate the programmed cell death pathway, but the cell will survive due to inhibition of one or more events along the pathway. Depending upon the point at which the cell survival polypeptide functions, the programmed cell death pathway can be inhibited early or relatively late within the execution of the cascade of events leading to ultimate cell death. Cell survival polypeptides and their encoding nucleic acids are well known in the art and include, for example, the Bcl-2 family of related proteins Bcl-2, BCl-$X_L$, Mcl-1, E1B-19K as well as inhibitors of the caspase activity such as p35, crmA and the dominant-negative forms of the caspases. These forms include, for example, caspase's with an inactivating mutation of the active site cysteine.

Overexpression of a cell survival polypeptide can be achieved using, for example, recombinant methods known to those skilled in the art. Routine procedures for performing such recombinant expression methods are described in, for example, Sambrook et al., *Molecular Cloning: A Laboratory Manual,* Cold Spring Harbor Laboratory, New York (1992), Greene Publishing Associates and Wiley-Interscience, New York, (1995). Such methods can be used to express stably or transiently a cell survival polypeptide at a level which is sufficient to prevent the induction of apoptosis. The nucleic acid molecule encoding the cell survival polypeptide can be encoded by, for example, a homologous nucleic acid derived from the same species or cell type, or alternatively, the nucleic acid molecule can be encoded by a heterologous nucleic acid derived from a different species or cell type. The source of the encoding nucleic acid is not important so long as the encoded cell survival polypeptide exhibits apoptosis inhibiting activity.

A level of expression of a cell survival polypeptide which is sufficient to prevent the induction of apoptosis is known to those skilled in the art and can also be routinely determined by those skilled in the art. Expression vectors and systems are known and commercially available which provide for recombinant polypeptide expression. It is a routine matter for one skilled in the art to choose a vector or system which will provide sufficient levels of expression in a particular host cell. Alternatively, the expression level sufficient to prevent the induction of apoptosis can be routinely determined by expressing the cell survival polypeptide and then measuring whether the cell survives after treatment with a pro-apoptotic agent.

In addition to recombinant methods of over-expressing a cell survival polypeptide, a cell can be used which inherently over-expresses a cell survival polypeptide. A specific example of a cell inherently over-expressing a cell survival polypeptide is the B cell lymphoma in which Bcl-2 was initially identified. This leukemia has a translocation of chromosome 14 to 18 causing high level expression of Bcl-2 and therefore cell survival. The leukemic phenotype is due to the increased cell survival. Other cell lines which inherently over-express a cell survival polypeptide can similarly be used in the methods of the invention.

The block from apoptosis due to over-expression of a cell survival polypeptide and the treatment of the cells with a pro-apoptotic agent provides antagonistic influences to the cell. In this way, the cells are essentially poised for programmed cell death. A pro-apoptotic agent can be a variety of different insults to the cell including, molecular, environmental and physical stimuli. As defined previously, such stimuli are known to those skilled in the art and can be characterized by activating a molecule within the apoptotic pathway. Examples of pro-apoptotic agents include inducers such as deprivation of a growth factor, Fas ligand, anti-Fas antibody, staurosporine, Tumor Necrosis Factor, ultraviolet and gamma-irradiation. Thus, treatment of a cell over-expressing a cell survival polypeptide with a pro-apoptotic agent will prime the cell for apoptosis since both positive and negative signals provide balancing effects. One advantage of this priming is that all cell death components are available for apoptosis once a signal is received that overcomes the lock of the cell survival polypeptide/anti-apoptotic agent. This allows for the rapid induction of apoptosis which can be use in screening for compounds that possess apoptosis inducing activity in the presence of Bcl-2 or Bcl-$X_L$. Such cells are particularly useful in screening for inhibitors of Bcl-2 or Bcl-$X_L$, respectively.

3. High Throughput

The methods described herein are also amenable to high throughput formats (e.g., a multi-well format assay where large numbers of samples can be screened rapidly and efficiently). For example, a 96-well format provides practical advantages since plates appropriate for manipulations and measuring devices are commercially available. Such procedures can be further automated to increase further the speed and efficiency of the method. These features, combined with the specificity of the method, allow for cell-free high throughput screening of candidate inhibitors or enhancers of caspase activity derived from membranes. For example, a library of test compounds can be administered to a plurality of membrane samples and then assayed for their ability to enhance or inhibit apoptosis. Identified compounds are valuable for both therapeutic and diagnostic purposes since they can allow for the treatment and detection of apoptotic mediated diseases. Such compounds are also valuable in research related to apoptotic mechanisms given that they can help deduce further molecular events and provide further specificity for the discovery and development of future compounds.

C. Caspase and Apoptotic Pathway Genes

As noted above, the invention provides assay methods relating to caspase and other apoptotic pathway genes and gene products, and methods for the use of the genes and gene products. In particular, the invention provides assays that detect modulation of membrane derived caspase activity. Given the disclosure provided herein, and the knowledge of those skilled in the art, an apoptotic pathway protein encoding gene can be isolated from a variety of cell types.

1. Isolation of Apoptotic Protein Encoding Genes

Apoptotic protein encoding genes may be isolated from either genomic DNA or preferably cDNA. Isolation of apoptotic pathway genes from genomic DNA or cDNA typically can proceed by, first, generating an appropriate DNA library through techniques for constructing libraries that are known in the art (see Sambrook et al., *Molecular Cloning: A Laboratory Manual,* Cold Spring Harbor Press, 1989) or purchased from commercial sources (e.g., Clontech, Palo Alto, Calif.). Briefly, cDNA libraries can be constructed in bacteriophage vectors (e.g., λZAPII), plasmids, or others, which are suitable for screening, while genomic DNA libraries can be constructed in chromosomal vectors, such as YACs (yeast artificial chromosomes), bacteriophage vectors, such as λEMBL3, λgt10, cosmids, or plasmids.

In one embodiment known apoptotic protein gene sequences (caspase, Bcl-2, Bcl-$X_S$, Bcl-$X_L$, Bik, Bad, Bax, etc.) may be utilized to design an oligonucleotide hybridization probe suitable for screening genomic or cDNA libraries. Preferably, such oligonucleotide probes are 20–30 bases in length. To facilitate hybridization detection, the oligonucleotide may be conveniently labeled, generally at the 5' end, with a reporter molecule, such as a radionuclide, (e.g., $^{32}P$), enzymatic label, protein label, fluorescent label, or biotin. Such libraries are then generally plated as phage or colonies, depending upon the vector used. Subsequently, a nitrocellulose or nylon membrane, to which the colonies or phage have been transferred, is probed to identify candidate clones which contain the apoptotic pathway gene. Such candidates may be verified as containing the target DNA by any of various means including, for example, DNA sequence analysis or hybridization with a second, non-overlapping probe.

Once a library is identified as containing an apoptotic protein gene, the gene can be isolated by amplification. Briefly, using a caspase gene as an illustration, when using cDNA library DNA as a template amplification primers are designed based upon known caspase gene sequences (see GenBank Accession Nos. X65019 (caspase-1), U13021 (caspase-2), U13737 (caspase-3), U25804 (caspase-4), U28015 (caspase-5), U20536 (caspase-6), U37448 (caspase-7), U60520 (caspase-8), U56390 (caspase-9), U60519 (caspase-10), and sequences available in the art). Amplification of cDNA libraries made from cells with high caspase activity is preferred. Primers for amplification are preferably derived from sequences in the 5' and 3' untranslated region in order to isolate a full-length cDNA. The primers preferably have a GC content of about 50% and contain restriction sites to facilitate cloning and do not have self-complementary sequences nor do they contain complementary sequences at their 3' end (to prevent primer-dimer formation). The primers are annealed to cDNA or genomic DNA and sufficient amplification cycles are performed to yield a product readily visualized by gel electrophoresis and staining. The amplified fragment is purified and inserted into a vector, such as λgt10 or pBS(M13+), and propagated. Confirmation of the nature of the fragment is obtained by DNA sequence analysis or indirectly through amino acid sequencing of the encoded protein.

Other methods may also be used to obtain the apoptotic pathway protein encoding nucleic acid molecule. For example, a nucleic acid molecule encoding caspase may be obtained from an expression library by screening with an antibody or antibodies reactive to caspase (see, Sambrook et al., *Molecular Cloning: A Laboratory Manual,* 2nd Ed., Cold Spring Harbor Laboratory Press, NY, 1987; Ausubel et al., *Current Protocols in Molecular Biology,* Greene Publishing Associates and Wiley-Interscience, NY, 1995).

Variants of apoptotic pathway protein genes may be engineered from natural variants (e.g., polymorphisms, splice variants, mutants), synthesized or constructed. Many methods have been developed for generating mutants (see, generally, Sambrook et al., supra; Ausubel, et a., supra, and the discussion above). Briefly, preferred methods for generating a few nucleotide substitutions utilize an oligonucleotide that spans the base or bases to be mutated and contains the mutated base or bases. The oligonucleotide is hybridized to complementary single stranded nucleic acid and second strand synthesis is primed from the oligonucleotide. The double-stranded nucleic acid is prepared for transformation into host cells, typically *E. coli,* but alternatively, other prokaryotes, yeast or other eukaryotes. Standard screening and vector growth protocols are used to identify mutant sequences and obtain high yields.

Similarly, deletions and/or insertions of genes may be constructed by any of a variety of known methods as discussed supra. For example, the gene can be digested with restriction enzymes and religated such that a sequence is deleted or religated with additional sequences such that an insertion or large substitution is made. Other means of generating variant sequences may be employed with methods known in the art, for example those described in Sambrook et al. (supra) and Ausubel et al. (supra). Verification of variant sequences is typically accomplished by restriction enzyme mapping, sequence analysis, or probe hybridization.

D. Vectors, Host Cells and Means of Expressing and Producing Protein

An apoptotic pathway protein may be expressed in a variety of host organisms. In certain embodiments, the protein is produced in bacteria, such as *E. coli,* or mammalian cells (e.g., CHO and COS-7), for which many expression vectors have been developed and are available. Other suitable host organisms include other bacterial species, and eukaryotes, such as yeast (e.g., *Saccharomyces cerevisiae*), and insect cells (e.g., Sf9).

A DNA sequence encoding the protein is introduced into an expression vector appropriate for the host. In certain embodiments, the protein can be is inserted into a vector such that a fusion protein is produced. As discussed above, the sequence may contain alternative codons for each amino acid with multiple codons. The alternative codons can be chosen as "optimal" for the host species. Restriction sites are typically incorporated into the primer sequences and are chosen with regard to the cloning site of the vector. If necessary, translational initiation and termination codons can be engineered into the primer sequences.

At a minimum, the vector must contain a promoter sequence. As used herein, a "promoter" refers to a nucleotide sequence that contains elements that direct the transcription of a linked gene and contains an RNA polymerase binding site. More typically, in eukaryotes, promoter sequences contain binding sites for other transcriptional factors that control the rate and timing of gene expression. Such sites include TATA box, CAAT box, POU box, AP1 binding site, and the like. Promoter regions may also contain enhancer elements. When a promoter is linked to a gene so as to enable transcription of the gene, it is "operatively linked."

Other regulatory sequences may be included. Such sequences include a transcription termination signal sequence, secretion signal sequence, origin of replication, selectable marker, and the like. The regulatory sequences are operationally associated with one another to allow transcription or translation.

The expression vectors used herein include a promoter designed for expression of the proteins in a host cell (e.g., bacterial). Suitable promoters are widely available and are well known in the art. Inducible or constitutive promoters are preferred. Such promoters for expression in bacteria include promoters from the T7 phage and other phages, such as T3, T5, and SP6, and the trp, lpp, and lac operons. Hybrid promoters (see, U.S. Pat. No. 4,551,433), such as lacVV, tac, and trc, may also be used. Promoters for expression in eukaryotic cells include the P10 or polyhedron gene promoter of baculovirus/insect cell expression systems (see, e.g., U.S. Pat. Nos. 5,243,041, 5,242,687, 5,266,317, 4,745,051, and 5,169,784), MMTV LTR, CMV IE promoter, RSV LTR, SV40, metallothionein promoter (see, e.g., U.S. Pat. No. 4,870,009) and the like.

The promoter controlling transcription of the apoptotic pathway protein may itself be controlled by a repressor. In some systems, the promoter can be derepressed by altering the physiological conditions of the cell, for example, by the addition of a molecule that competitively binds the repressor, or by altering the temperature of the growth media. Preferred repressor proteins include, but are not limited to the *E. Coli* lacI repressor responsive to IPTG induction, the temperature sensitive λcI857 repressor, and the like.

In other preferred embodiments, the vector also includes a transcription terminator sequence. A "transcription terminator region" has either a sequence that provides a signal that terminates transcription by the polymerase that recognizes the selected promoter and/or a signal sequence for polyadenylation.

Preferably, the vector is capable of replication in the host cells. Thus, when the host cell is a bacterium, the vector preferably contains a bacterial origin of replication. Preferred bacterial origins of replication include the p15A, pSC101, and col E1 origins of replication, especially the ori derived from pUC plasmids. In yeast, ARS or CEN sequences can be used to assure replication. A well-used system in mammalian cells is SV40 ori.

The plasmids also preferably include at least one selectable marker that is functional in the host. A selectable marker gene includes any gene that confers a phenotype on the host that allows transformed cells to be identified and selectively grown. Suitable selectable marker genes for bacterial hosts include the ampicillin resistance gene (Amp$^r$), tetracycline resistance gene (Tc$^r$) and the kanamycin resistance gene (Kan$^r$). The kanamycin resistance gene is presently preferred. Suitable markers for eukaryotes usually require a complementary deficiency in the host (e.g., thymidine kinase (tk) in tk- hosts). However, drug markers are also available (e.g., G418 resistance and hygromycin resistance).

One skilled in the art appreciates that there are a wide variety of suitable vectors for expression in bacterial cells and which are readily obtainable. Vectors such as the pET series (Novagen, Madison, Wis.), the tac and trc series (Pharmacia, Uppsala, Sweden), pTTQ18 (Amersham International plc, England), pACYC 177, pGEX series, and the like are suitable for expression of the protein. Baculovirus vectors, such as pBlueBac (see, e.g., U.S. Pat. Nos. 5,278,050, 5,244,805, 5,243,041, 5,242,687, 5,266,317, 4,745,051, and 5,169,784; available from Invitrogen, San Diego) may be used for expression in insect cells, such as *Spodoptera frugiperda sf*9 cells (see, U.S. Pat. No. 4,745,051). The choice of a bacterial host for the expression of an apoptotic pathway protein is dictated in part by the vector. Commercially available vectors are paired with suitable hosts.

A wide variety of suitable vectors for expression in eukaryotic cells are available. Such vectors include pCMVLacI, pXT1 (Stratagene Cloning Systems, La Jolla, Calif.); pCDNA series, pREP series, pEBVHis (Invitrogen, Carlsbad, Calif.). In certain embodiments, the gene of interest is cloned into a gene targeting vector, such as pMC1neo, a pOG series vector (Stratagene Cloning Systems).

The apoptotic pathway protein is isolated by standard methods, such as affinity chromatography, size exclusion chromatography, metal ion chromatography, ionic exchange chromatography, HPLC, and other known protein isolation methods. (see generally Ausubel et al. supra; Sambrook et al. supra). An isolated protein gives a single band on SDS-PAGE when stained with Coomassie blue.

Apoptotic pathway proteins may be expressed as a hexahis $(His)_6$ fusion protein and isolated by metal-containing chromatography, such as nickel-coupled beads. Briefly, a sequence encoding $His_6$ is linked to a DNA sequence encoding the desired protein. Although the $His_6$ sequence can be positioned anywhere in the molecule, preferably it is linked at the 3' end immediately preceding the termination codon. The fusion may be constructed by any of a variety of methods.

E. Use of Inhibitors or Enhancers

Inhibitors and enhancers may be used in the context of this invention to exert control over the cell death process or cytokine activation (e.g., IL-1, which is activated by caspase-1). Thus, these inhibitors and enhancers will have utility in diseases characterized by either excessive or insufficient levels of apoptosis. Inhibitors of proteases have potential to treat the major neurodegenerative diseases: stroke, Parkinson's Disease, Alzheimer's Disease, and ALS. As well, caspase protease inhibitors may be used to inhibit apoptosis in the heart following myocardial infarction, in the kidney following acute ischemia, and in diseases of the liver. Enhancers of caspase activity may be used in contexts when apoptosis or cytokine activation are desired. For example, inducing or increasing apoptosis in cancer cells or aberrantly proliferating cells may be effected by delivery of a caspase enhancer.

The inhibitors and enhancers may be her coupled with a targeting moiety that binds a cell surface receptor specific to the cells. Administration of inhibitors or enhancers will generally follow established protocols. The compounds identified by the methods of the instant invention may be administered either alone, or as a pharmaceutical composition. Briefly, pharmaceutical compositions of the present invention may comprise one or more of the inhibitors or enhancers as described herein, in combination with one or more pharmaceutically or physiologically acceptable carriers, diluents or excipients. Such compositions may comprise buffers such as neutral buffered saline, phosphate buffered saline and the like, carbohydrates such as glucose, mannose, sucrose or dextrans, mannitol, proteins, polypeptides or amino acids such as glycine, antioxidants, chelating agents such as EDTA or glutathione, adjuvants (e.g., aluminum hydroxide) and preservatives. In addition, pharmaceutical compositions of the present invention may also contain one or more additional active ingredients.

Compositions identified by the methods of the present invention may be formulated for the manner of administration indicated, including for example, for oral, nasal, venous, intracranial, intraperitoneal, subcutaneous, or intramuscular administration. Within other embodiments of the invention, the compositions described herein may be administered as part of a sustained release implant. Within yet other embodiments, compositions of the present invention may be formulized as a lyophilizate, utilizing appropriate excipients which provide stability as a lyophilizate, and subsequent to rehydration.

As noted above, pharmaceutical compositions also are provided by this invention. These compositions may contain any of the above described inhibitors, enhancers, DNA molecules, vectors or host cells, along with a pharmaceutically or physiologically acceptable carrier, excipients or diluents. Generally, such carriers should be nontoxic to recipients at the dosages and concentrations employed. Ordinarily, the preparation of such compositions entails combining the therapeutic agent with buffers, antioxidants such as ascorbic acid, low molecular weight (less than about 10 residues) polypeptides, proteins, amino acids, carbohydrates including glucose, sucrose or dextrins, chelating agents such as EDTA, glutathione and other stabilizers and excipients. Neutral buffered saline or saline mixed with nonspecific serum albumin are exemplary appropriate diluents.

In addition, the pharmaceutical compositions of the present invention may be prepared for administration by a variety of different routes, including for example intraarticularly, intracranially, intradermally, intrahepatically, intramuscularly, intraocularly, intraperitoneally, intrathecally, intravenously, subcutaneously or even directly into a tumor. In addition, pharmaceutical compositions of the present invention may be placed within containers, along with packaging material which provides instructions regarding the use of such pharmaceutical compositions. Generally, such instructions will include a tangible expression describing the reagent concentration, as well as within certain embodiments, relative amounts of excipient ingredients or diluents (e.g., water, saline or PBS) which may be necessary to reconstitute the pharmaceutical composition. Pharmaceutical compositions are useful for both diagnostic or therapeutic purposes.

Pharmaceutical compositions of the present invention may be administered in a manner appropriate to the disease to be treated (or prevented). The quantity and frequency of administration will be determined by such factors as the condition of the patient, and the type and severity of the patient's disease. Dosages may be determined most accurately during clinical trials. Patients may be monitored for therapeutic effectiveness by appropriate technology, including signs of clinical exacerbation, imaging and the like.

The following examples are offered by way of illustration, and not by way of limitation.

EXAMPLES

Example 1

Cell-Lines and Cell Culture 697 human lymphoblastoid cells stably infected with a retroviral expression construct containing Bcl-2 cDNA (697-Bcl-2 cells) or a control neomycin resistance gene (697-neo-cells) (Miyashita and Reed, 1993) (obtained from Dr. John Reed, Burnham Institute) were used in these studies. The cells were maintained in mid-log phase growth in RPMI 1640 medium (Irvine Scientific, Santa Ana, Calif.) supplemented with 10% fetal bovine serum ((FBS) Hyclone, Logan, Utah), 0.2 mg/ml G-418 (Gibco, Gaithersburg, Md.) and 0.1 mg/ml penicillin/streptomycin (Irvine Scientific). Murine dopaminergic MN9D cells (obtained from Dr. A. Heller, University of Chicago) were grown in DMEM medium (Irvine Scientific) supplemented with 10% FBS, 2 mM glutamine and 0.1 mg/ml penicillin/streptomycin. Mouse brain cortical cells were prepared at E15 of gestation in Hark's buffered saline solution (Irvine Scientific) with 15 mM HEPES. The tissue was briefly dissociated with 0.1% trypsin and washed thoroughly with MEM medium supplemented with 10% FBS and 0.4 mg/ml DNase I (Sigma, St. Louis, Mo.), gently triturated and flash frozen.

Example 2

Sub-Cellular Fractionation

Frozen cell pellets containing $\approx 10^9$ cells were thawed and resuspended in cold hypotonic buffer (10 mM Na-HEPES, 5 mM $MgCl_2$, 42 mM KCl, pH 7.4) supplemented with 1 mM PMSF, 1 µg/ml leupeptin, 1 µg/ml pepstatin A, 5 µg/ml aprotinin, 0.1 mM EDTA, 0.1 mM EGTA and 5 mM DTT (Sigma) to a density of $\approx 1.5 \times 10^8$ cells/ml. The samples were incubated on ice for 30 min at which time the cells were lysed using 30–40 strokes with a Dounce homogenizer. The sample was centrifuged twice for 10 min at 500×g, 4° C. to separate the nuclei. The nuclear pellets were then washed twice in the same buffer supplemented with 1.6M sucrose, yielding the nuclear fraction. The supernatant was then centrifuged at 14,000×g for 30 min at 4° C. to pellet the heavy membranes. The heavy membranes were washed 3 times with 1.5 ml cold hypotonic buffer containing protease inhibitors and DTT. The washed membranes were resuspended in hypotonic buffer so that the total protein concentration was approximately 2 mg/ml, yielding the heavy membrane fraction, that was either flash frozen or used immediately for enzymatic measurements without freezing. The 14,000×g supernatant was centrifuged at 100,000×g for 30 min at 4° C., yielding a supernatant (cytoplasmic fraction) and a pellet (light membrane fraction). Protein concentrations were measured using Protein Assay Kit II from BioRad with bovine serum albumin as the calibration standard. In some experiments, cell pellets were lysed as above, but without a freezing step. To test effects of cytochrome c on caspase activity, some samples were treated with 10 µg/ml bovine cytochrome c (Sigma Chemical, St. Louis, Mo.) throughout the entire isolation procedure. In some experiments, mitochondrial fractions were prepared from lysed 697-neo and 697-Bcl-2 cells by the rat liver mitochondrial methods of Mancini and collaborators (Mancini, et al., 1998) and used without freezing.

Example 3

Immunoblotting

Subcellular fractions (50 µg protein per lane) were resolved by SDS-PAGE on 12% or 16% gels (Novex, La Jolla, Calif.) and transferred to Immobilon PVDF membranes (Millipore, Bedford, Mass.). Membranes were blocked in PBS/0.1% Tween 20 (PBST)+0.4% casein (I-block, Tropix, Bedford, Mass.). Blots were incubated in 1 µg/ml primary antibody diluted in PBST/casein for 1 hour. Following three washes in PBST, blots were incubated for one hour in 1:15,000 dilutions of alkaline phosphatase conjugated goat antirabbit IgG or goat anti-mouse IgG (Tropix) in PBST/casein. Blots were then washed twice with PBST, twice in assay buffer (10 mM diethanolamine, pH 10.0, 1 mM $MgCl_2$) and then incubated in 250 µM chemiluminescent substrate CSPD (Tropix) in assay buffer and exposed to Biomax film (Kodak, Rochester, N.Y.) overnight.

In some cases, following the secondary antibody incubations, the blots were washed with 10 mM Tris, pH9.5, 1 mM $MgCl_2$. The blots were then incubated for 30 minutes in 1.25 µg/ml DDAO phosphate (Amersham, Arlington Heights, Ill.) dissolved in the Tris buffer. The blots were scanned using the STORM fluorescence imager (Molecular Dynamics, Sunnyvale, Calif.). The antibodies used were against Bcl-2 (Transduction Labs, Lexington, Ky.), caspase-3 (Srinivasan, et al., 1998), cytochrome c (Pharmingen, San Diego, Calif.), cytochrome oxidase, subunit IV (Molecular Probes, Portland, Oreg.), D4-GDP dissociation inhibitor (D4-GDI) (a gift of Dr. G. Bokoch, Scripps Research Institute, La Jolla, Calif.) and poly(ADP-ribose) polymerase (PARP) (Enzyme Systems, Livermore, Calif.).

Example 4

Activity Assays

Caspase activity was measured by mixing 50 µl of an enzyme-containing fraction and 200 µl of 25 µM DEVD-amc (Asp-Glu-Val-Asp-aminomethylcoumarin) substrate in ICE buffer (20 mM HEPES, 1 mM EDTA, 0.1% CHAPS, 10% sucrose, 5 mM DTT, pH 7.5) in duplicate Cytoplate wells. Product formation was monitored by the increase in fluorescence (ex=360 nm, em=460 nm) over 1–2 hours at 30° C. using the CytoFluor 4000 plate reader (Perseptive Biosystems, Framingham, Mass.). For kinetic studies, the substrate concentration was varied in the range 1–100 µM. For inhibition studies the enzyme was pretreated with 150 µl inhibitor for 30 min at room temperature prior to the addition of 50 µl of 50 µM substrate solution. Inhibitor $IC_{50}$ values were determined using the equation:

$$\Delta FL/\Delta t = (\Delta FL/\Delta t)_o/(1+[I]/IC_{50})$$

$\Delta FL/\Delta t$ is the observed initial rate of fluorescence change at inhibitor concentration [I] and $(\Delta FL/\Delta t)_o$ is the initial rate fluorescence change for the uninhibited enzyme.

Example 5

Activation Assays

Heavy membrane samples were diluted to 1 mg/ml in hypotonic buffer or in 0.25 M sucrose, 10 mM MOPS, 2 mM EDTA, pH 7.4 (Mancini, et al., 1998) containing 5 mM DTT with or without 1% NP-40. Caspase activation was induced by adding either 60–160 ng/ml recombinant murine caspase-1 (in bacterial lysate), 2 µg/ml of purified human granzyme B (Enzyme Systems Products, Livermore, Calif.) or buffer, and incubating the samples for 60 min at 30° C. or 37° C. After the activation period, the heavy membrane pellet was removed from the sample by centrifugation for 10 min at 14,000×g at 4° C. The DEVD-amc cleaving activities in the resulting supernatants were corrected for the activity of the exogenous enzymes. To examine the time course of spontaneous activation of caspase activity from membranes, 50 µl of heavy membrane slurry containing 50–100 µg total protein was mixed with 200 µl hypotonic buffer containing 25 μM DEVD-amc substrate and 6 mM DTT in 96 well Cytofluor plates and fluorescence was measured over time. At selected time points, aliquots were removed from some wells, centrifuged for 10 min at 14,000×g to remove the heavy membranes and the supernatant was added back into the 96 well plate to measure the soluble DEVD-amc cleavage activity. In some experiments, subcellular fractions were treated with 1 μg/ml bovine cytochrome c (Sigma) and 50 μM dATP (New England Biolabs, Beverly, Mass.) (final concentrations) for 40 min at 30° C. prior to measurement of caspase activity.

Example 6

Recombinant Caspase Production

BL21 (DE3) cells harboring a plasmid containing the cloned human caspase-3 cDNA (Fernandes-Alnemri, et al., 1994) (provided by Dr. E. Alnemri, Thomas Jefferson University) was ligated into the Bam HI/Xho I sites of pET21b (Novagen, Madison, Wis.) and were grown in one liter LB medium containing 0.1 mg/ml ampicillin at 37° C. When the culture density reached $A_{600}=1$, IPTG (Sigma) was added to a concentration of 1 mM and the culture was incubated at 25° C. for three hours. The cells were harvested by centrifugation at 2,000×g for 15 min at 4° C. The cells were lysed using one freeze-thaw cycle in 100 ml Binding buffer (20 mM TrisCl, 500 mM NaCl, 5 mM imidazole, 0.1% triton X-100) with 0.1 mg/ml lysozyme. Cell debris was removed from the sample by centrifugation at 20,000× g, for 30 min at 4° C. The lysed cells were treated just prior to centrifugation with $MgCl_2$ and DNase I to reduce viscosity. The supernatant was filtered through a 0.45 μm syringe filter and loaded onto a 1 ml $Ni+^2$-charged HiTrap Chelating column (Amersham Pharmacia, Uppsala, Sweden) at a 1 ml/min flow rate. The column was washed at 1 ml/min with 10 ml Binding buffer followed by 10 ml Binding Buffer containing 60 mM imidazole. The caspase-3 protein was eluted from the column using a 30 ml linear gradient of imidazole (60–500 mM).

Recombinant murine caspase-1 was expressed using BL21 (DE3) pLys S cells harboring pET3ap30mICEFLAG plasmid (a generous gift of Drs. H. R. Horvitz and Ding Xue, MIT) which contains the p30 caspase-1 cDNA inserted into the Nde I/BamH I sites of the pET3a expression vector (Novagen). A three liter culture was grown at 37° C. in Induction medium (20 g/l tryptone, 10 g/l yeast extract, 6 g/l NaCl, 3g/l $Na_2HPO_4$, 1 g/l KH2PO4, 1 mM $MgCl_2$, 0.1 mM $CaCl_2$, pH 7.4) containing 0.1 mg/ml ampicillin and 0.025 mg/ml chloramphenicol. When the culture reached a density of $A_{600}=1.0$, IPTG was added to 1 mM and the culture was shaken at 25° C. for 3 hours. The cells were collected by centrifugation at 2000×g for 15 min at 4° C. and resuspended in 100 ml cold buffer containing 25 mM TrisCl, pH 8.0, 25 mM KCl, 0.1 % triton X-100, and 0.1 mg/ml lysozyme (InovaTech, Abbottsford, B.C., Canada). The cells were lysed using one freeze/thaw cycle and lysate was clarified by treating the sample with 0.02 mg/ml DNase I, 0.5 mM $MgCl_2$ (Sigma) for 60 min and then centrifuging at 20,000×g for 30 min at 4° C. to remove cell debris.

Example 7

In Vitro Translation of Caspases $^{35}$S-labeled caspases (wild-type) are obtained by in vitro translation in the presence of $^{35}$S-methionine using a coupled transcription/translation system in rabbit reticulocyte lysate using TNT Kit (Promega) according to the manufacturer's recommendations.

Example 8

Characterization of Subcellular Fractions

Subcellular fractions were prepared from 697 cells stably infected with retroviral constructs expressing either Bcl-2 cDNA or a neomycin resistance gene (697-Bcl-2 and 697-neo cells, respectively) (Miyashita and Reed, 1993). Nuclear, heavy membrane, light membrane, and cytosolic fractions were isolated from these cells, and characterized by Western blot analysis with antibodies specific for proteins with distinct known subcellular distributions, as in Example 3. Antibodies used were directed against cytochrome oxidase, specific for mitochondrial inner membrane (Tzagoloff, 1982), poly(ADP-ribose) polymerase (PARP), specific for nuclei (Berger, 1985), D4-GDP dissociation inhibitor (D4-GDI), specific for cytoplasm (Na, et al., 1996) and Bcl-2. The immunoblots were visualized on film by chemiluminescense, except the cytochrome oxidase immunoblot which was visualized by chemifluorescence.

As shown in FIG. 1, the mitochondrial marker was found almost exclusively in the heavy membrane fraction, the nuclear marker only in the nuclear fraction, and the cytoplasmic marker only in the cytoplasmic fraction. Thus, the fractionation methods employed generated fractions with the expected subcellular distribution of marker proteins. Importantly, cytoplasmic contamination of the nuclear and membrane fractions could not be detected, and only minimal mitochondrial contamination of nuclear fractions was detected (the diffuse D4-GDI reactive band in the nuclear fraction shown in FIG. 1 is non-specific). Western analysis of fractions from 697-neo cells with an antibody to human Bcl-2 (FIG. 1) demonstrated strong reactivity in nuclear and heavy membrane fractions, weaker reactivity in the light membrane fraction, and undetectable signal in cytoplasm, in accord with previous results (Krajewski, et al., 1993; Yang, et al., 1995; Lithgow, et al., 1994). Similar analysis of fractions from 697-Bcl-2 cells showed significant overexpression.

Example 9

Subcellular Distribution of Cleavage Activity

Figure 2A:
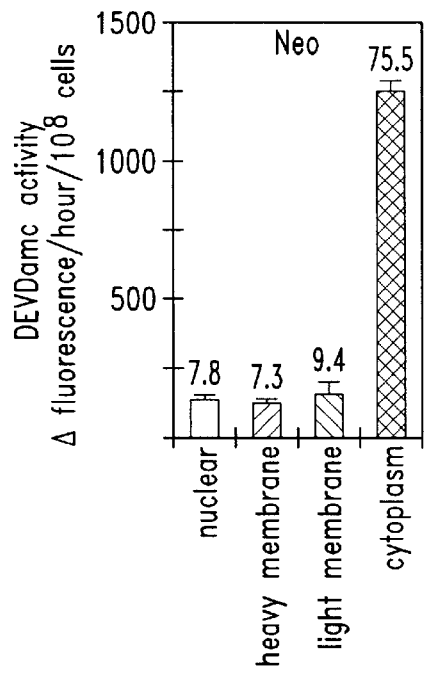
FIGS. 2A–D are histograms of caspase substrate cleavage activity in subcellular fractions.
Figure 2B:
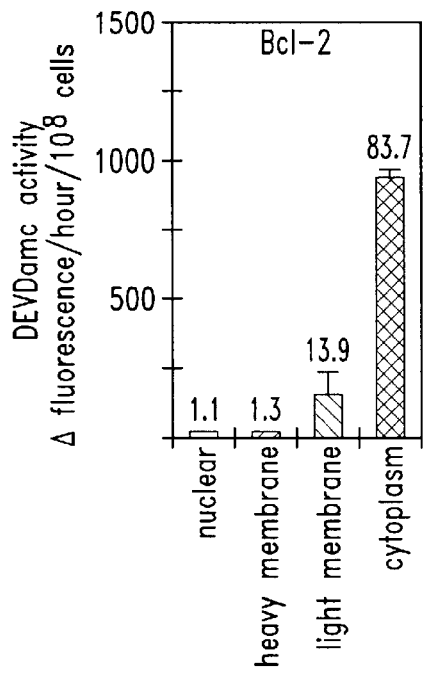
Figure 2C:
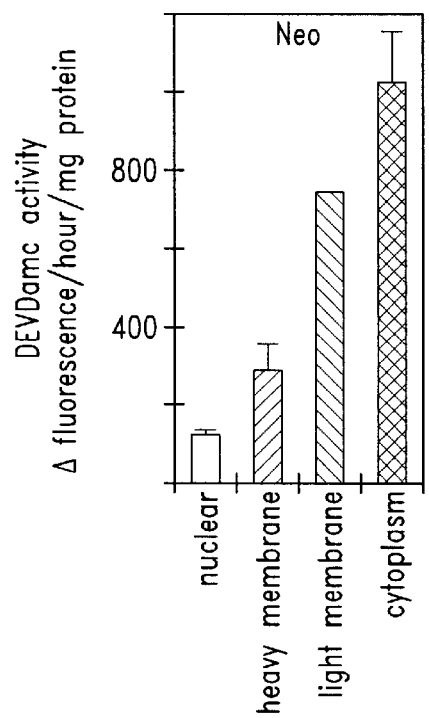
Figure 2D:
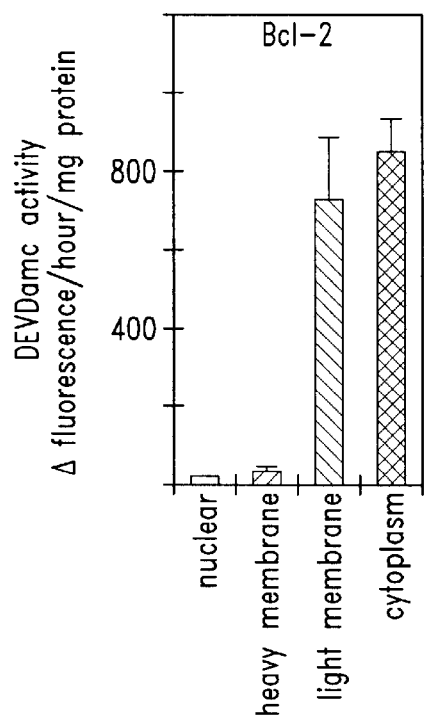

Preliminary experiments indicated that caspase activity was associated with membranes derived from unstimulated cells. To determine the subcellular distribution of such caspases, caspase activity in the subcellular fractions from 697-neo cells was quantitated by incubating them with the substrate DEVD-amc, and measuring the increase in fluorescence over the subsequent 2 hours. DEVD-amc is a useful substrate for all caspases characterized to date, with the exception of caspase-2 (Talanian et al., 1997; and data not shown). While most of the DEVD-amc cleavage activity (~75%) was in the cytoplasmic fraction, a substantial amount of the cleavage activity was found in the nuclear, heavy membrane and light membrane fractions (FIGS. 2A and 2C). DEVD-amc cleavage activity in subcellular fractions of 697 cells transfected with neo control or Bcl-2 expression vectors were fractionated and the caspase activity of each subcellular fraction was assayed. The observed cleavage activity values in the histogram are normalized for constant number of cells (FIGS. 2A–2B) or mg protein (FIGS. 2C–2D). The values listed for each column in A and B indicate the percent of total cleavage activity present in each fraction. The error bars in FIGS. 2A–2D indicate the range of observed values for two independent 697 cell preparations.

The major DEVD-amc cleaving activity in each fraction was indeed caspase activity since it was potently blocked by specific caspase inhibitors (Table I, column 1 Example 13, and data not shown).

Example 10

Bcl-2 Suppression of Membrane-Derived Caspase Activity

We next examined the effect of Bcl-2 on the caspase activities in the various subcellular fractions. When subcellular fractions derived from 697-Bcl-2 cells were prepared and incubated with DEVD-amc substrate, substantially reduced caspase activity was observed in the nuclear and heavy membrane fractions compared with 697-neo cells (FIG. 2B). This Bcl-2 effect was evident when the caspase activity was measured on a per cell basis or per mg protein and resulted in an 80–90% reduction in caspase activity in these fractions (FIGS. 2B and 2D). The effect of Bcl-2 expression on caspase activity in these fractions was specific, since little if any suppression was seen in the activities observed in the cytoplasmic or light membrane fractions (FIGS. 2A–2D). These observations suggested that the membrane-associated caspase activity was not simply derived from a small percentage of apoptotic cells in the 697-neo cultures whose numbers were suppressed in the 697-Bcl-2 cultures. If that were the case, one would also have expect to see major differences in caspase activities between cytoplasmic fractions derived from 697-neo vs. 697-Bcl-2 cells. Indeed, control experiments demonstrated that when 697-neo cells were induced to undergo apoptosis by staurosporine treatment, the major increase in caspase activity was found in the cytoplasm (data not shown).

The ability of Bcl-2 to suppress membrane-associated caspase activity was not limited to the 697 lymphoblastoid cells, since similar effects were observed in Jurkat T cells and FL5.12 cells (data not shown). Since the present data, as well as other published studies, have demonstrated that Bcl-2 protein is found predominantly in nuclear envelope and heavy membrane fractions (FIG. 1; Krajewski et al., 1993; Yang et al., 1995), the present results were compatible with the possibility that Bcl-2 might act locally to regulate this membrane-derived caspase activity. In an effort to begin analyzing such mechanisms, we further characterized this membrane-derived, Bcl-2-suppressible caspase activity and focused our efforts on the heavy membrane fraction.

Example 11

Figure 3A:
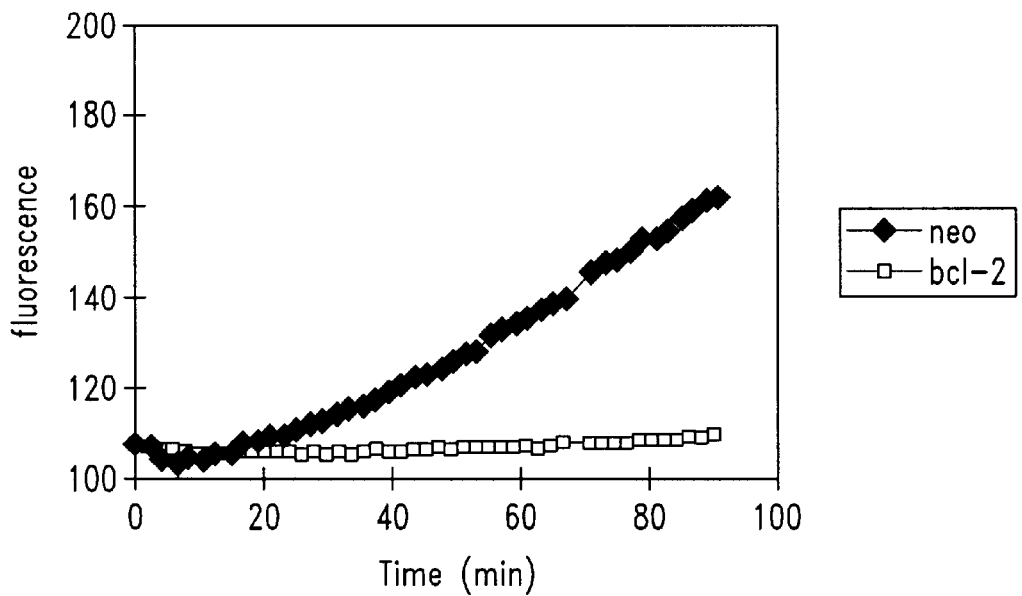
FIGS. 3A and 3B are graphs representing membrane-associated procaspase-3 spontaneous activation.
Figure 3B:
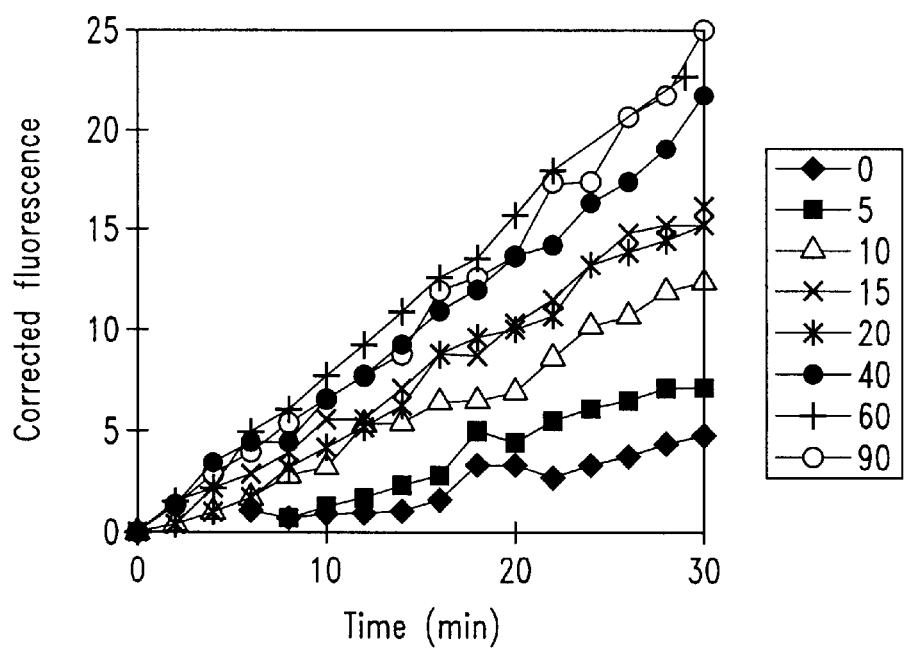

Spontaneous Activation and Membrane Release of Membrane-Derived Caspase Activity It was possible that the membrane associated caspase activity was due either to an active membrane-bound enzyme, or alternatively, to the spontaneous activation and release of a soluble active enzyme. Therefore a set of experiments was designed to distinguish between these two possibilities. First, to freshly prepared heavy membranes derived from 697-neo cells (neo-membranes), hypotonic buffer and DEVD-amc substrate at room temperature was immediately added, and the emergence of amc fluorescence over a 90 minute period (FIG. 3A) was measured. The DEVD-amc cleavage activity of was measured by adding 20 $\mu$g of freshly prepared membranes into hypotonic buffer containing 20 $\mu$M DEVD-amc (final concentration). The evolution of amc product was measured by the change in fluorescence (ex=360 nm, em=460 nm) at room temperature. The data demonstrate that there is little detectable fluorescence change over the first 15 minutes of incubation, but after this lag period, the rate of amc production increases markedly (FIG. 3A). These results indicated that the freshly prepared membranes did not contain active caspase, but that activation occurred spontaneously during the incubation period. To assess whether this newly activated caspase was soluble or membrane bound, membranes were incubated for different periods of time (0 to 90 minutes), following which the samples were centrifuged for 10 minutes at 14,000×g at 10° C. and the resulting supernatants were assayed for caspase activity with DEVD-amc substrate. These data demonstrated that very little caspase activity was present in the supernatant initially, but that soluble caspase activity appeared thereafter (FIG. 3B). Quantitative analysis of these data demonstrated that for each supernatant, fluorescence increased linearly, indicating that once released from the membranes, no further activation occurred. Furthermore, the slopes of these curves (FIG. 3B) approximate the instantaneous slopes of the corresponding time points in the progress curve for the heavy membrane slurry (FIG. 3A). Therefore, all of the caspase-3 activity can be accounted for in the supernatant fraction, indicating that all active enzyme had been released from the membranes. In contrast to the neo-membranes, membranes derived from the 697-Bcl-2 cells (Bcl-2-membranes) failed to generate significant DEVD-amc cleaving activity (FIG. 3A).

Example 12

Procaspase-3 Presence in Heavy Membranes

Figure 4:
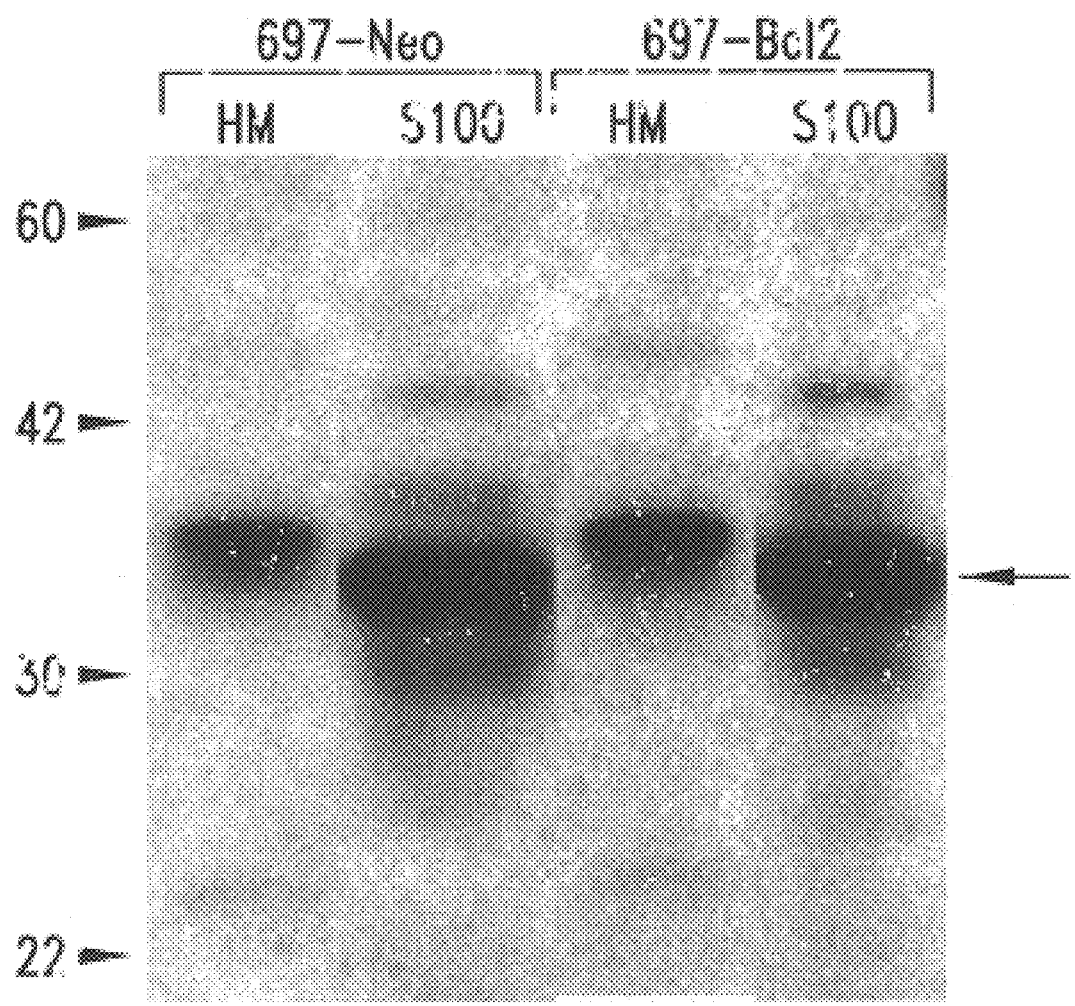
FIG. 4 is a scanned image of an immunoblot representing SDS-PAGE analysis of heavy membrane and cytosolic fractions from 697-neo and 697-Bcl-2 cells, probed with an anti-caspase-3 polyclonal antibody. The arrowheads indicate the migration of protein size markers (Rainbow Markers, Novex); the arrow indicates procaspase-3. HM=heavy membrane fractions; S100=cytosolic fraction.

The lack of DEVD-amc cleaving activity in the Bcl-2-membranes could be due either to the absence of activatable procaspase or suppression of procaspase activation. To distinguish between these alternatives, first, Western blot analysis was performed on the membrane and cytosolic fractions with antibodies specific for caspase-3 (Example 3), since the measured DEVD-amc cleavage activity is in fact due to caspase-3 (see below). The results (FIG. 4) demonstrate the presence of a caspase-3 reactive band that is of similar intensity in both the neo-membranes and Bcl-2-membranes, and that is approximately the size expected for the procaspase zymogen. Interestingly, the electrophoretic mobility of the membrane-derived bands was slightly slower than that of cytoplasmic procaspase-3.

Figure 5:
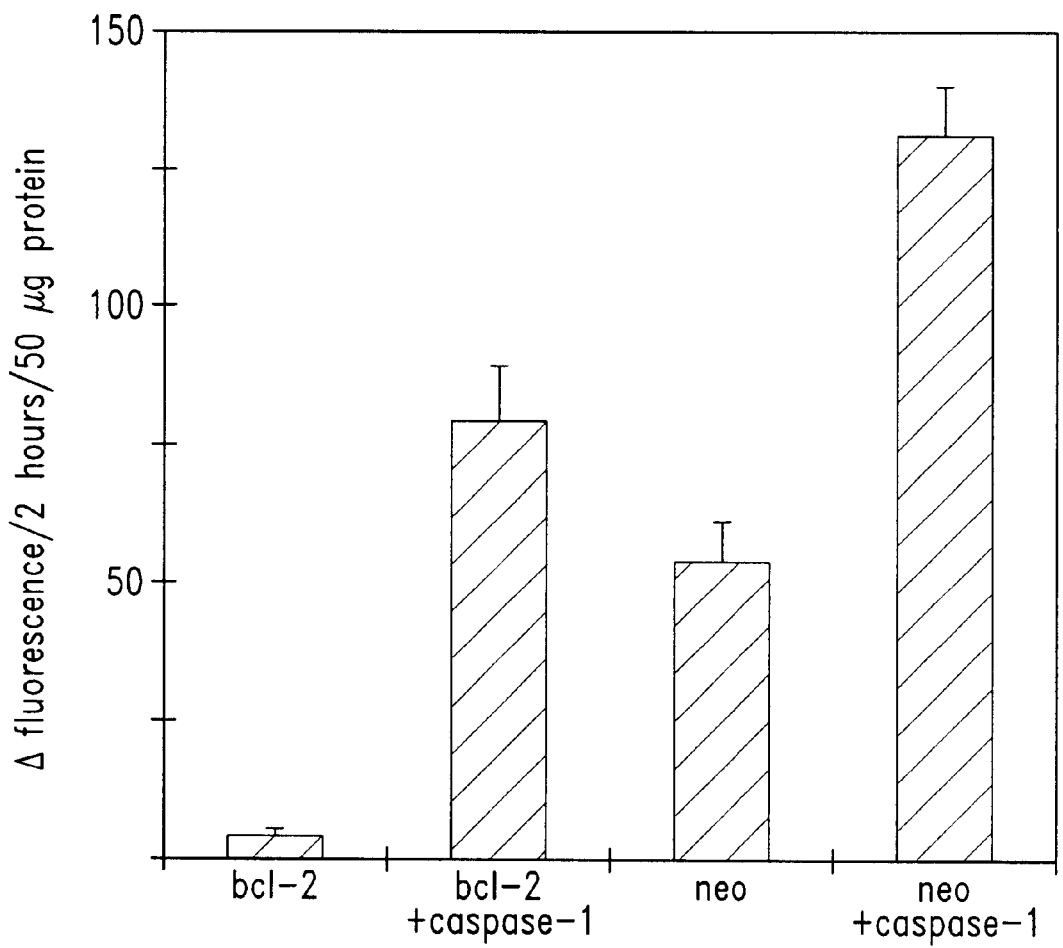
FIG. 5 is a graph illustrating activation of membrane associated DEVD-amc cleavage activity by exogenous caspase-1.

To further demonstrate the presence of procaspase-3 in both neo- and Bcl-2-membranes, we attempted to activate these fractions by treatment with exogenous caspase-1, since procaspases can be activated by proteolytic cleavage at aspartic acid residues between their large and small subunits (Srinivasula et al., *Proc. Natl. Acad. Sci. USA* 93:14486–14491, 1996; Stennicke and Salvesen, *J. Biol. Chem.* 272:25719–25723, 1997; Salvesen and Dixit, *Cell* 91:443–446, 1997). As we have shown above, membranes derived from Bcl-2 cells showed almost no caspase activity when measured under our standard conditions. However, treatment of the Bcl-2-membranes with caspase-1 caused a robust induction of enzymatic activity (FIG. 5). In this experiment, heavy membrane fractions (containing 50 $\mu$g total protein) from 697-Bcl-2 and 697-neo cells were re-suspended and treated with murine caspase-1 for one hour at room temperature. Following centrifugation, the DEVD-amc cleavage activity of the resulting supernatant was measured. The DEVD-amc cleavage activity of caspase-1 treated samples was corrected for exogenous caspase-1 activity by subtracting the fluorescence of control samples containing only caspase-1 from the observed fluorescence. The error bars in FIG. 5 represent the standard deviation of the observed values in 3 independent experiments. The neo-membranes were also activated by exogenous caspase-1. But importantly, following activation, the resulting caspase activities from the Bcl-2- and neo-membranes were always similar, within a factor of two (FIG. 5). Together with the procaspase-3 immunoblot data, this supports the conclusion that comparable levels of procaspase-3 are present in neo- and Bcl-2-membranes.

Caspase-1 treatment of membranes not only activated the endogenous caspase activity, but also released it from the membranes, since the activity remained in the supernatant when the membranes were removed by centrifugation (FIG. 5). This induction and release were due to the proteolytic activity of caspase-1, since the caspase-1 activation could be completely blocked by 200 nM acYVAD-aldehyde which inhibits caspase-1, but not the membrane caspase, at this concentration (data not shown). These results indicate that both neo- and Bcl-2-expressing cells contain similar amounts of a membrane-associated inactive procaspase that can be activated by caspase-1. However, without exogenous caspase treatment, only membranes derived from the neo-expressing cells demonstrated spontaneous caspase activation.

Example 13

Characterization of Induced and Spontaneous Caspase Activities

The membrane-derived caspase activities were further characterized by measuring the inhibition of DEVD-amc cleavage by several peptide aldehyde inhibitors (Table I). The $IC_{50}$ values for the inhibition of DEVD-amc activity derived from activated Bcl-2-membranes are quite similar to those for the inhibition of the activity derived from neo-membranes, suggesting that caspase-1 activates the same procaspase in both membrane preparations. Furthermore, these $IC_{50}$ values are similar to those for the spontaneously activated DEVD-amc activity derived from neo-membranes, suggesting that the spontaneous and caspase-1-induced activities derive from the same caspase. In all cases, the inhibition data fit well to a simple competitive inhibition curve, suggesting that each DEVD-amc activity arose from a single caspase rather than a mixture of enzymes. The observed $IC_{50}$ values for the membrane associated caspases are very similar to those for purified fully-processed recombinant human caspase-3. Kinetic measurements also indicate that $K_m$ values for hydrolysis of DEVD-amc by the membrane-derived caspases (10 μM) are similar to that observed with fully processed caspase-3 (Nicholson et al., Nature 376:37–43, 1995). N-terminal microsequence analysis of activated, affinity purified heavy membrane caspase confirms that this enzyme is indeed human caspase-3.

TABLE I

Heavy membrane (HM) derived caspases from various cell types and recombinant human caspase-3: Inhibition by peptide aldehydes

| | $IC_{50}$ (nM) | | | | | |
|---|---|---|---|---|---|---|
| inhibitor | 697-neo HM (spontaneous activity) | 697-neo HM (caspase-1 treated) | 697 Bcl-2 HM (caspase-1 treated) | cortical cell HM (caspase-1 treated) | MN9D HM (caspase-1 treated) | r-caspase-3 (His)$_6$ |
| DEVD-ald | 2.3 | 2.8 | 1.3 | 1.0 | 0.72 | 1.0 |
| DFLD-ald | 3.4 | 4.5 | 3.6 | 2.3 | 2.5 | 1.5 |
| YVAD-ald | >10,000 | >10,000 | >10,000 | >10,000 | >10,000 | >10,000 |

To determine if the presence of membrane-associated caspase activity is a general property of mammalian cells, the DEVD-amc cleavage activity in heavy membranes from two other cell sources was measured: mouse E 15 primary brain cortical cells and the mouse dopaminergic MN9D cell line (Choi et al., Neurobiology 89:8943–8947, 1992). Heavy membrane fractions were prepared using identical procedures to those used for the 697 cells and were activated with caspase-1. These fractions contained a membrane-associated caspase activity with similar cleavage activities per mg protein as observed in 697 cells (data not shown) and that was blocked by caspase inhibitors with a similar potency to that observed with fractions derived from 697 cells or with recombinant caspase-3 (Table I). Accordingly, the existence of membrane-derived caspase activity is not specific to 697 cells, but appears to be a more general phenomenon.

Example 14

Exogenous Cytochrome C and Membrane Associated Procaspace-3

Figure 6A:
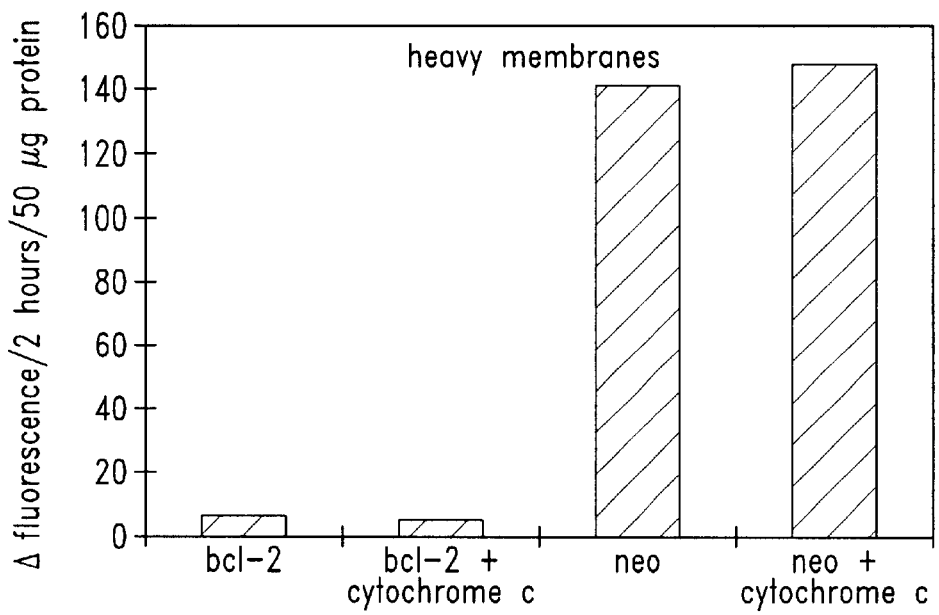
FIGS. 6A and 6B are graphical representations of DEVD-amc cleavage activity in 697-neo and 697-Bcl-2 cells in the presence and absence of cytochrome c.

Several recent reports have shown that the release of cytochrome c from mitochondria can cause the activation of cytoplasmic caspase-3 (Liu et al., Cell 86:147–157, 1996; Li et al., Cell 91:479–489, 1997). Other reports have demonstrated that cytochrome c is released from mitochondria following apoptotic insults and that Bcl-2 can inhibit that release (Kluck et al, Science 275:1132–1136, 1997; Yang et al, Science 275:1129–1132, 1997). Thus, it was possible that the difference observed between caspase activities in heavy membranes from Bcl-2- and neo-expressing cells simply reflected inhibition by Bcl-2 of cytochrome c release during preparation of the heavy membrane fractions or during subsequent incubation of these fractions. To investigate this possibility, cell fractionation was performed in the presence of exogenous cytochrome c and measured whether this influenced caspase activation. If the Bcl-2-membranes had low caspase activity because of a Bcl-2 effect on cytochrome c sequestration, then the addition of exogenous cytochrome c during membrane fractionation should increase the caspase activity derived from those membranes to the levels seen in membranes from neo-cells. Accordingly, during the fractionation procedure for heavy membranes from neo- and Bcl-2-expressing cells, following Dounce homogenization, the sample was split into two fractions. One fraction was processed with standard buffers, while to the other fraction 10 μg/ml of bovine cytochrome c was added, and 10 μg/ml to the buffers used to suspend and wash the heavy membranes. This concentration of cytochrome c was chosen since it represents the estimated total amount of cytochrome c present in the starting cell pellets (Li et al., *J. Biol. Chem.* 272:30299–30305, 1997). Finally, these membranes were resuspended in 1 µg/ml cytochrome c plus 50 µM dATP, incubated, and then assayed for DEVD-amc cleaving activity. Aliquots of the cytochrome c-treated heavy membranes and cytoplasmic fractions were then incubated with hypotonic buffer containing 50 pM dATP/1 µg/ml cytochrome c for 40 min at 30° C., while the membranes and cytoplasmic samples that had not been treated with cytochrome c were incubated only with buffer. Each sample was then centrifuged, and DEVD-amc cleavage activity in the supernatant was measured. The data in FIG. 6 represents three equivalent experiments (FIG. 6A). This activity was compared to that from our usual membrane preparations prepared without cytochrome c, and incubated without cytochrome c or dATP.

Figure 6B:
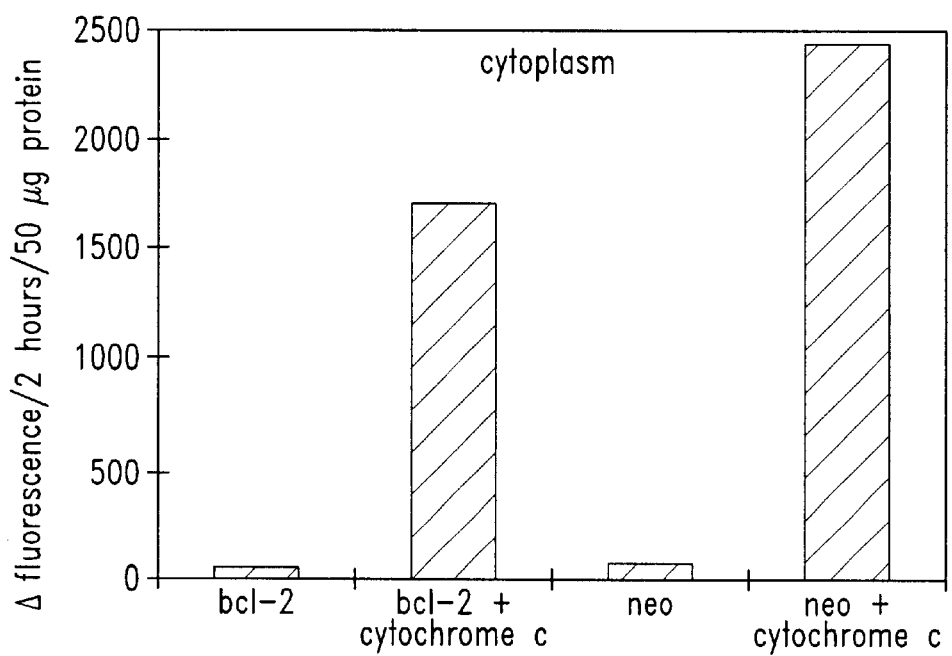

The data demonstrate that inclusion of cytochrome c during membrane fractionation and incubation has no effect on membrane-derived caspase activity; the activity in the membranes derived from Bcl-2-expressing cells remained low compared to the activity in the neo-membranes, and furthermore, there was also no effect of cytochrome c on the caspase activity derived from the neo-membranes (FIG. 6A). Although the cytochrome c treatments did not activate the membrane-associated caspase, the enzyme could still be activated by subsequent treatment with exogenous caspase-1 (data not shown). The lack of a cytochrome c effect on the activation of the membrane caspase was not due to an inactive preparation of cytochrome c, since the DEVD-amc cleavage activity of the cytoplasmic fractions from both neo and Bcl-2 cells were strongly activated by inclusion of cytochrome c during fractionation and assay (FIG. 6B). Therefore, Bcl-2 expression suppresses the activation of the membrane-associated procaspase-3, but this effect is not overcome by addition of exogenous cytochrome c. Furthermore, Bcl-2 overexpression did not affect the ability of cytochrome c to activate caspase-3 in cytoplasmic fractions.

Example 15

Release of Membrane-Derived Caspase is not Via Simple Leakage from Organelles

A recent report described the presence of procaspase-3 in the intermembrane space within mitochondria (Mancini et al., *J. Cell Biol.* 140:1485–1495, 1998). Thus, it was possible that this material could account for the activatable caspase activity that was measured in the mitochondria-containing heavy membrane fractions. Furthermore, it was possible that the spontaneous activity that was measured in membrane fractions from 697-neo cells was due to leakage of active caspase from mitochondria, and that mitochondria isolated from 697-Bcl-2 cells were simply less leaky (Yang et al., *Science* 275:1129–1132, 1997). However, several experiments suggested that the activity measured was not due to leakage from mitochondria, and that the activity is distinct from that described by Mancini et al.,supra.

Figure 7A:
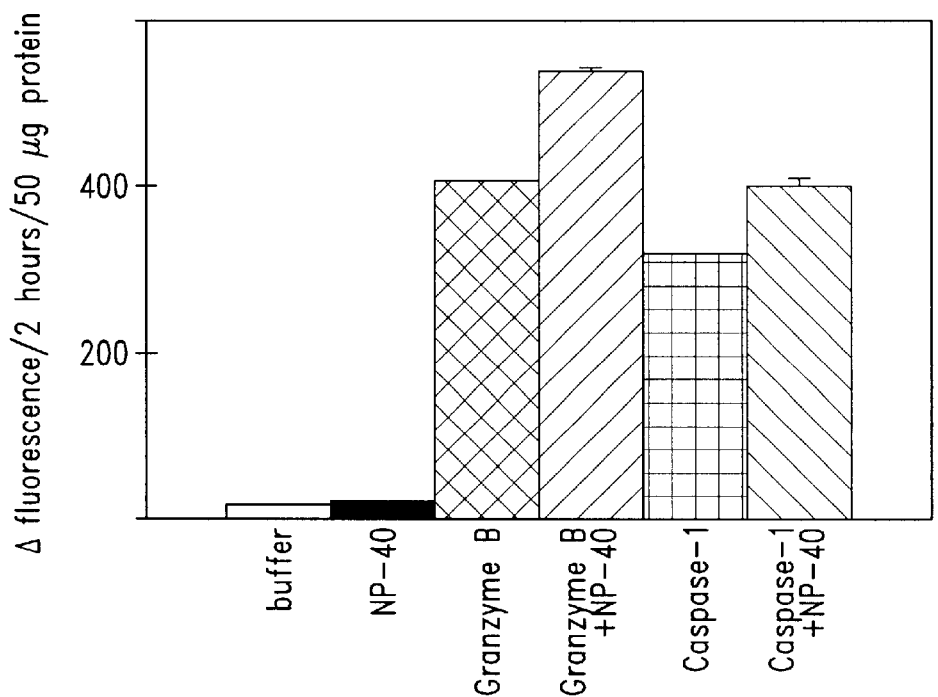
FIGS. 7A, 7B, and 7C are graphs representing the effects of permeabilizing detergents on membrane-associated caspase activity.
Figure 7B:
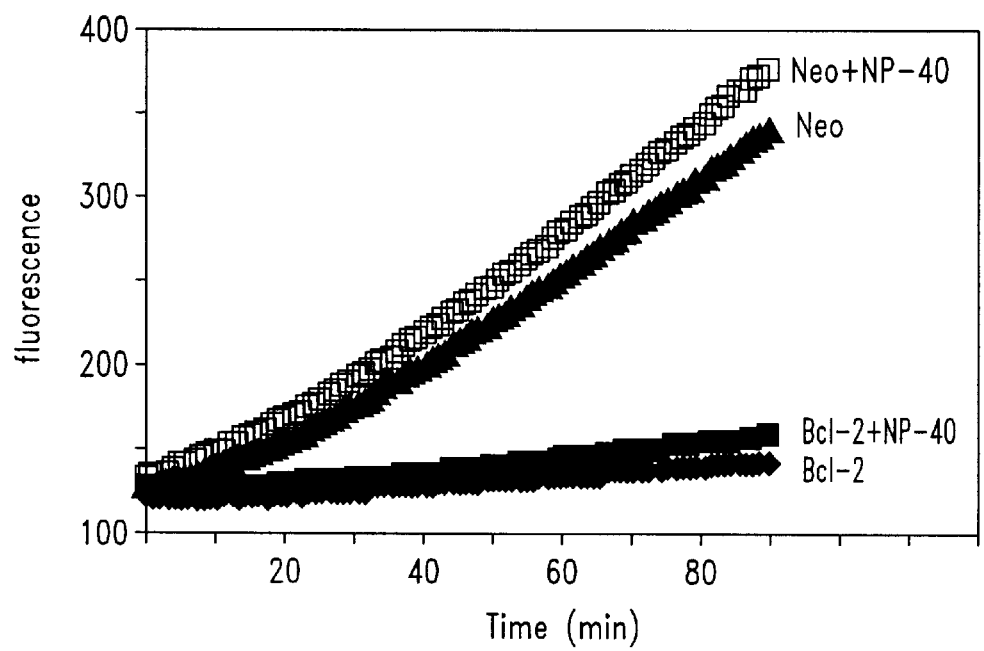

First, whether the addition of 1% NP-40 to neo-membranes affected the level of either spontaneous activity or the activity induced by caspase-1 or granzyme B was tested. It was reasoned that if procaspase and/or active caspase was sequestered within organelles, then enhanced activity would be measured in the presence of NP-40. Treatment with 1% NP-40 was sufficient to release almost all of the cytochrome c present in heavy membrane preparations (data not shown). Furthermore, it was shown by Mancini and colleagues that treatment of their mitochondrial preparations with 1% NP-40 allowed granzyme B to cleave procaspase-3 whereas no cleavage was observed in the absence of detergent (Mancini et al., *J. Cell Biol.* 140:1485–1495, 1998). However, the present results demonstrate that 1% NP-40 had little effect either on spontaneous activity or the activity induced by treatment with caspase-1 or granzyme B (FIG. 6A). In this experiment, 160 µl of neo-membranes were diluted with 180 µl hypotonic buffer and treated with 40 µl 10% NP-40 detergent or dH$_2$O (final vol=380 µl). The diluted membranes were activated by the addition of 20 µl granzyme B or caspase-1 lysate or buffer, and incubated for 60 min at 30° C. Following activation, the heavy membranes were removed by centrifugation and the DEVD-amc cleaving activity of each sample was measured by adding 50 µl of each supernatant to 200 µl of 25 µM DEVD-amc substrate in ICE buffer (FIG. 7A).

Next, to analyze whether membrane preparations from 697-Bcl-2 cells may have low spontaneous activity due to enhanced sequestration of a caspase, we added DEVD-amc to Bcl-2- and neo-membrane preparations, incubated them in buffer alone or buffer plus 1% NP-40, and measured the appearance of fluorescence. In this experiment, the effect of NP-40 on the progress curve for heavy membrane catalyzed DEVD-amc hydrolysis was measured by adding 50 µl freshly prepared neo- or Bcl-2-membranes to 200 µl 25 uM DEVD-amc in hypotonic buffer pH 7.5 (containing 4 mM DTT) with or without 1% NP-40 detergent. The results indicate that 1% NP-40 had only a minor effect on the magnitude or rate of fluorescence increase. Preparations derived from 697-Bcl-2 cells had low activity regardless of whether 1% NP-40 was present, demonstrating that this low level of activity was not due to sequestration of an active caspase.

Figure 7C:
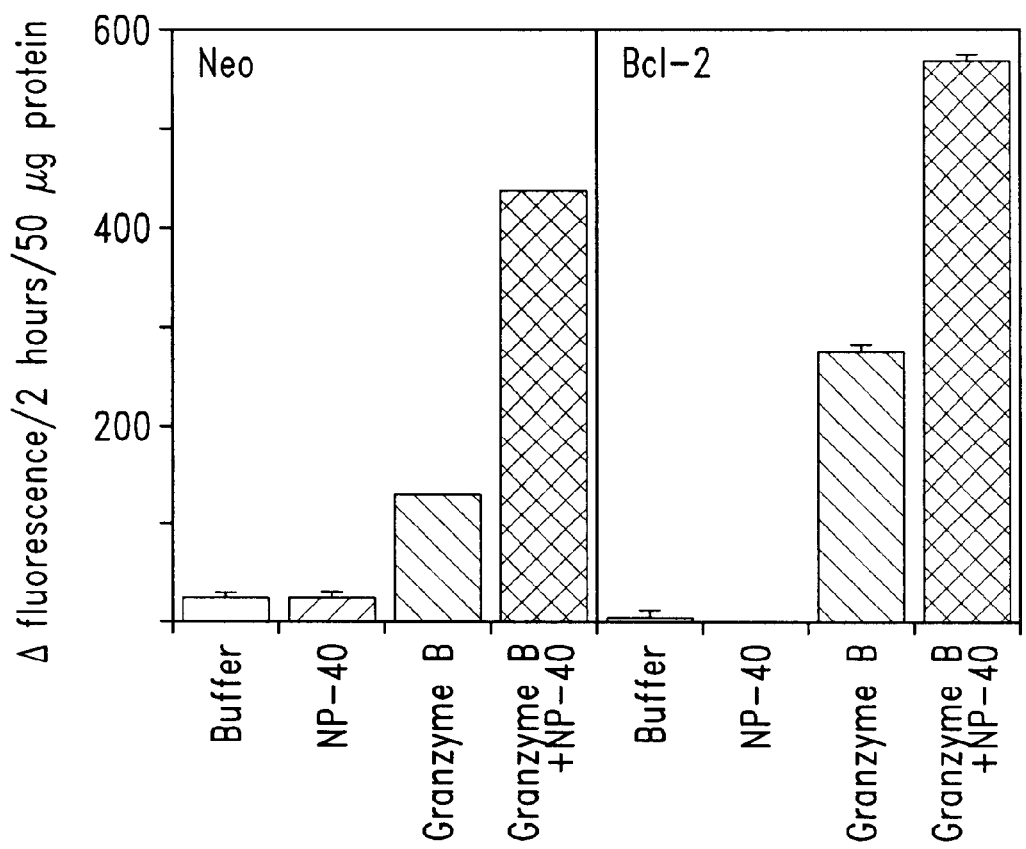

Lastly, mitochondrial fractions from 697-neo and 697-Bcl-2 cells were prepared using the methods described by Mancini et al (1998) to more directly assess the relationship between our results and their published data. In this experiment, diluted membranes, with or without 1% NP-40, were activated by the addition of granzyme B or buffer for 60 min, centrifuged, and assayed for DEVD-amc cleavage activity as described in FIG. 7A. As shown in FIG. 7C, fractions from both 697-neo and 697-Bcl-2 made by these methods have granzyme B-activatable caspase activity in the absence of NP-40. However, in the presence of 1% NP-40, granzyme B treatment yielded enhanced caspase activity. Thus, under these conditions, granzyme B generates caspase activity in both NP-40 independent and dependent manners.

From the foregoing it will be appreciated that, although specific embodiments of the invention have been described herein for purposes of illustration, various modifications may be made without deviating from the spirit and scope of the invention. Accordingly, the invention is not limited except as by the appended claims.

What is claimed is:

1. A method for identifying an inhibitor of the activity of a membrane derived caspase, comprising contacting a membrane fraction with a caspase substrate in the presence and absence of at least one candidate inhibitor, wherein said membrane fraction is derived from cells not undergoing apoptosis; and comparing the levels of caspase substrate turnover, and therefrom identifying an inhibitor of the activity of a membrane derived caspase.

2. The method of claim 1, wherein the caspase substrate comprises a site cleaved by a caspase selected from the group consisting of a protein, a polypeptide, an oligopeptide, a peptide mimetic and a peptide.

3. The method of claim 2, wherein the substrate comprises the peptide DEVD.

4. The method of claim 1, wherein the membrane fraction is prepared from un-stimulated tissue culture cells selected from the group consisting of 697 lymphoblastoid cells, E15 primary brain cortical cells, MN9D cells, Jurkat T cells, and FL5.12 cells.

5. The method of claim 1, wherein the membrane fraction comprises membranes selected from the group consisting of heavy membranes and nuclear membranes.

6. The method of claim 1, wherein the membrane fraction comprises heavy membranes.

7. The method of claim 1, wherein substrate turnover is detected by time course analysis.

8. The method of claim 1, wherein substrate turnover is detected by endpoint analysis.

9. The method of claim 7 or 8, wherein caspase substrate turnover detection is performed by a method selected from the group consisting of fluorescence spectroscopy, mass spectrometry, HPLC, colorimetry, fluorography, radiography, gel electrophoresis, chromatography and N-terminal peptide sequencing.

10. The method of claim 1, wherein the membrane fraction is derived from cells expressing pro-apoptotic polypeptides.

11. The method of claim 1, further comprising incubating the membrane fraction with a caspase activator prior to or concurrent with the addition of the caspase substrate.

12. The method of claim 1, wherein the membrane fraction is derived from cells treated with a stimulator of apoptosis.

13. The method of claim 12, wherein the stimulator of apoptosis is selected from the group consisting of deprivation of a growth factor, staurosporine, anti-fas antibody, ultraviolet irradiation, gamma irradiation and Tumor Necrosis Factor.

* * * * *